United States Patent
Zebaze et al.

(10) Patent No.: US 11,462,302 B2
(45) Date of Patent: Oct. 4, 2022

(54) METHOD AND APPARATUS FOR IDENTIFYING AND QUANTIFYING ABNORMALITY

(71) Applicant: Straxcorp Pty Ltd, Melbourne (AU)

(72) Inventors: Roger Zebaze, Coburg (AU); Yu Peng, Box Hill (AU)

(73) Assignee: Straxcorp Pty Ltd, Melbourne (AU)

( * ) Notice: Subject to any disclaimer, the term of this patent is extended or adjusted under 35 U.S.C. 154(b) by 825 days.

(21) Appl. No.: 16/081,701

(22) PCT Filed: Feb. 28, 2017

(86) PCT No.: PCT/AU2017/050172
§ 371 (c)(1),
(2) Date: Aug. 31, 2018

(87) PCT Pub. No.: WO2017/147648
PCT Pub. Date: Sep. 8, 2017

(65) Prior Publication Data
US 2021/0217162 A1 Jul. 15, 2021

(30) Foreign Application Priority Data
Mar. 3, 2016 (AU) ................................ 2016900806

(51) Int. Cl.
*G06T 7/00* (2017.01)
*G16B 20/00* (2019.01)
(Continued)

(52) U.S. Cl.
CPC ............ *G16B 45/00* (2019.02); *G06T 7/0012* (2013.01); *G16B 20/00* (2019.02); *G16H 10/40* (2018.01);
(Continued)

(58) Field of Classification Search
None
See application file for complete search history.

(56) References Cited

U.S. PATENT DOCUMENTS

| 9,633,108 B2 * | 4/2017 | Nachev ................ G06K 9/6284 |
| 2005/0085705 A1 * | 4/2005 | Rao .................... G01N 33/6896 |
| | | 702/19 |

(Continued)

FOREIGN PATENT DOCUMENTS

| JP | 2005-198970 A | 7/2005 |
| JP | 2013-504341 A | 2/2013 |

(Continued)

OTHER PUBLICATIONS

International Search Report and Written Opinion of the International Searching Authority for International Patent Application No. PCT/AU2017/050172 dated May 11, 2017, 8 pages.

(Continued)

*Primary Examiner* — Soo Shin
(74) *Attorney, Agent, or Firm* — Merchant & Gould P.C.

(57) ABSTRACT

A method of building an abnormality quantifier comprising: generating at least one selected first dataset comprising measurements of a normal population or sample and at least one second selected dataset comprising measurements of an abnormal population or sample; generating an image or map by imagizing the datasets; identifying a normality zone within the image or map using the first dataset; identifying an abnormality zone within the image or map using the second dataset; determining a definition of abnormality based on a comparison of the normality zone and the abnormality zone; receiving or accessing at least one third dataset comprising measurements of a both known normal and abnormal population or sample; testing the performance of the initially defined abnormality against one or more (Continued)

preset performance criteria; and outputting an abnormality quantifier when optimal performance has been reached.

24 Claims, 11 Drawing Sheets

(51) Int. Cl.
    *G16B 40/00*     (2019.01)
    *G16B 45/00*     (2019.01)
    *G16H 10/40*     (2018.01)
    *G16H 30/20*     (2018.01)
    *G16H 50/20*     (2018.01)
    *G16H 50/70*     (2018.01)

(52) U.S. Cl.
    CPC ............. *G16H 30/20* (2018.01); *G16H 50/20* (2018.01); *G06T 2207/10072* (2013.01); *G06T 2207/30008* (2013.01); *G16B 40/00* (2019.02)

(56) References Cited

U.S. PATENT DOCUMENTS

| | | | |
|---|---|---|---|
| 2005/0169517 A1* | 8/2005 | Kasai | G06T 7/0012 |
| | | | 382/128 |
| 2012/0232375 A1* | 9/2012 | Zebaze | G06T 7/70 |
| | | | 600/407 |
| 2013/0044927 A1* | 2/2013 | Poole | G06T 7/0014 |
| | | | 382/128 |
| 2013/0324861 A1* | 12/2013 | Ando | A61B 5/7275 |
| | | | 600/483 |
| 2016/0042287 A1* | 2/2016 | Eldardiry | G06Q 50/22 |
| | | | 706/14 |
| 2017/0124478 A1* | 5/2017 | Baradaran | G06N 20/00 |

FOREIGN PATENT DOCUMENTS

| | | | |
|---|---|---|---|
| WO | 2011/029153 A1 | 3/2011 | |
| WO | 2012/013920 A1 | 2/2012 | |
| WO | WO-2012013920 A1 * | 2/2012 | ............. G06F 16/30 |

OTHER PUBLICATIONS

Extended European Search Report for European Patent Application No. 17759003.1 dated Feb. 18, 2019, 10 pages.

Varun, C. et al., "Anomaly detection: A survey", ACM Computing Surveys, 41(3): 1-58 (2009).

Examination Report for European Patent Application No. 17759003.1 dated Mar. 31, 2021, 14 pages.

Yao, J. et al., "Cortical shell unwrapping for vertebral body abnormality detection on computed tomography", Computerized Medical Imaging and Graphics, 38(7): 628-638 (Apr. 2014).

* cited by examiner

METHOD AND APPARATUS FOR IDENTIFYING AND QUANTIFYING ABNORMALITY

RELATED APPLICATION

This application is a National Stage Application of PCT/AU2017/050172, filed 28 Feb. 2017, which claims the benefit of the filing and priority dates of Australian patent application no. 2016900806 filed 3 Mar. 2016, the contents of which are incorporated herein by reference in their entireties. To the extent appropriate, a claim of priority is made to each of the above disclosed applications.

FIELD OF THE INVENTION

The present invention relates to a method and apparatus for identifying and quantifying abnormality, such as between two or more co-measurements, and is of particular but by no means exclusive application in the analysis of biological samples such as bone. The invention also relates to a method and system for building an abnormality quantifier, such as using two or more co-measurements, also of particular but by no means exclusive application in the analysis of biological samples.

BACKGROUND OF THE INVENTION

In many fields, it is necessary to characterize and identify the distinction between a normal sample group and an abnormal, such as to determine whether any particular individual member of that group (e.g. a person, product, geophysical reading, etc) is abnormal. This typically involves, first, measuring the sample using a suitable device, then analysing the measurement results, typically using statistical methods, to determine whether it is abnormal. In the field of healthcare (though also in many non-medical areas), for example, defining a reference range or reference interval of physiologic measurement in healthy persons is commonly required. This is relevant to the interpretation of test or other results as a frame of reference for a particular subject. For example, subjects within the reference range may be regarded as normal and those outside the reference range as abnormal (e.g. as diseased). That is, the reference range—in this example—is defined by a parameter with upper and lower limits delineating what is regarded as normal, with abnormal being indicated by values above or below, respectively, these upper and lower limits.

Several techniques are currently used to capture or define a reference range for a specific biological or non-biological characteristic. For example, the reference range that characterizes normality may be defined by two values between which 95% of the presumed reference group fall; it is assumed that 2.5% of normal subjects—though indeed normal—will have values of the reference parameter that overlaps with the range of abnormal individuals, such that 2.5% of normal subjects will have a value of this parameter below the lower limit of the normal interval. Likewise, 2.5% of the normal subjects will have a value of this parameter higher than the upper limit. In a sense, therefore, in this analysis 5% of the normal population will be presumed to be abnormal but, more correctly, 5% of the normal population is presumed to have values of the characterizing parameter that are indicative of abnormality, even though that 5% forms a part of the normal population.

In another example, normal and abnormal are defined as the number of standard deviations above or below the mean value of the 'normal' reference population. This may be applied in bone medicine. In the case of osteoporosis or fragile bone, abnormal is defined as having a bone mineral density less than −2.5 Standard Deviation below the mean value of a young normal healthy population.

In the field of lipids medicine, normal or abnormal LDL (low-density lipoprotein) levels are defined based on different percentile values: less than 20% is considered as abnormally low whereas greater than 95% of the reference population is considered abnormally high.

Sometimes an additional consideration in defining a reference range and hence what is normal and abnormal arises from the shape of the relevant population's distribution curve. In some cases a log-normal distribution rather than arithmetic normal distribution is used and thresholds are based on the selected distribution and/or selected transformed distribution curve. Regardless of the shape of the curve, values used to define normal versus abnormal are still chosen based on thresholds such as an absolute number, $\sigma$, or percentiles.

However, there are a number of problems with existing approaches to defining these reference ranges and hence normal versus abnormal. For example, commonly only one side of a range may be of interest, so—in effect—a 'one-sided' definition is used. This is so with certain markers of pathologies: cancer antigen 19-9 is generally regarded as having no clinical significance if below what is usual in the normal population; BMD (in the field bone), if above a certain value, is automatically considered normal. Therefore, such markers are often provided with only one limit of the reference range stated.

In another approach, values of a given parameter either above a specified percentile (e.g., 5th percentile) or below a specified percentile (e.g., 95th percentile) are considered indicative of abnormality; subjects with values between these percentiles are considered normal. This 'two-sided' definition is used, for example, to define normal blood pressure, normal tissue mineralization, and normal height. In the case of blood pressure, 'normal' corresponds—for example—to a systolic blood pressure of between 120 and 80 mm Hg; in the case of tissue mineralization, 'normal' corresponds to mineralization values (ash fraction) between 62% and 68%.

Regardless of whether the reference range is defined using a one-sided or two-sided approach, the distinction between normal and abnormal may still not be well captured. For example, a height of 160 m may be within a normal range (that is, within the upper and lower limit of normality) for an individual of 70 kg, but abnormal for an individual of 120 kg. Age is intrinsically linked to BMD, as is porosity to tissue mineral density. Thus, lower and upper values of the references range may not fully distinguish normal from abnormal. A value may still fall within the upper and lower values but yet be abnormal because some other determinant of the value makes it abnormal but these other determinants of the measurement of interest are not considered. As a consequence, existing techniques may not—in some case—reliably facilitate the identification of the disease, its causes, pathogenesis, a physiological manifestation, or the effects of influential factors (such as a treatment) that may cause a sample or a subject to be more or less normal, or move from a normal state to an abnormal state or vice versa.

SUMMARY OF THE INVENTION

According to a first broad aspect of the invention, there is provided a method of building an abnormality quantifier, the method comprising:

generating at least one first selected dataset comprising measurements of a normal population or sample and at least one second selected dataset comprising measurements of an abnormal population or sample;

generating an image or map by imagizing the datasets (i.e., converting a dataset into an image or map), such as by converting geometric virtual coordinates representative of a dataset into an image resulting in a cloud of points representative of normal or abnormal subjects;

identifying a normality zone within the image using the first dataset;

identifying an abnormality zone within the image using the second dataset;

determining a definition of abnormality (such as a geometric definition based on shape, direction and/or orientation) based on a comparison of the normality zone and the abnormality zone (including measures thereof);

receiving or accessing at least one third dataset comprising measurements of a both known normal and abnormal population or sample;

testing the performance of the initially defined abnormality against one or more preset performance criteria; and outputting an abnormality quantifier when optimal performance has been reached;

wherein the measurements of the normal population or sample and the measurements of the abnormal population comprise co-measurements (such as two- or more dimensional ordered pairs of co-measurements, of either co-dependent or non co-dependent parameters).

In an embodiment, the method comprises obtaining the measurements of the normal population or sample by measuring one or more normal samples or subjects, and obtaining the measurements of the abnormal population or sample by measuring one or more abnormal samples or subjects.

The comparison of the normality zone and the abnormality zone may be based on representative points of the respective zones, such as the midpoint of the normality zone and the maximum abnormal point (or 'MAP') of the abnormality zone.

It will be appreciated by the skilled person that the image or map generated by imagizing the datasets need not actually be displayed, but is in a form that may be displayed as an image or map (whether stored in a single file or in a plurality of files).

In an embodiment, the method includes optimizing the performance by modifying the definition of abnormality.

Measuring the sample or population may comprise acquiring images using computed tomography (CT), magnetic resonance imaging (MRI) or other imaging device, and processing the images using an image processing technique, such as the one disclosed in WO 2011/029153 or any other image processing device.

Measuring the sample may comprise processing previously acquired images using an image processing technique such as the one disclosed in WO 2011/029153 or any other image processing device.

Measuring the sample may comprise analysing a biological sample using an analysis technique, such as an assay. Measuring the sample may comprise obtaining measurements using a measurement instrument. Measuring the sample may comprise analysing a biological sample using an analysis technique comprising an assay. Measuring the sample may comprise obtaining measurements using a measurement instrument comprising an assay measuring instrument.

The sample may be a biological sample. The abnormality may be obesity. The sample may comprise bone.

In an embodiment, the measurement device is an imaging device. The sample may be bone and the measurement device may be configured to output a plurality of different sets of bone parameters.

In another embodiment, the bone abnormality is fracture-vulnerability. The fracture-vulnerability may be due to structural abnormality comprising a reduced amount of bone. In one example, the method further comprises estimating a timeframe (e.g. 2 years) in which a fracture may occur from an amount of bone reduction.

In another example, the method further comprises recategorizing a subject that has previously been categorized (such as by BMD) by adjusting the definition of abnormality (such as abnormality threshold). A previous categorization by BMD may be, for example, osteopenia or normal BMD. Such subjects may be 70 years of age or older. The abnormality may be age dependent.

In another embodiment, the fracture vulnerability is due to brittleness.

In a further embodiment, the method further comprises determining a type of fracture-vulnerability including distinguishing fracture-vulnerability due to reduced amount of bone from fracture-vulnerability due to bone brittleness. The method may further comprise applying a treatment according to the type of fracture-vulnerability, or changing a treatment based on the type of fracture-vulnerability (where changing the treatment may comprise ceasing an existing treatment and commencing a new treatment, or modifying an existing treatment).

The treatment may be a romosuzumab, abaloparatide, teriparatide or other anabolic therapy, or a Denosumab, Alendronate or other antiresorptive therapy.

The method may comprise identifying one or more abnormalities in one or more measurements of the sample. The method may comprise applying, a treatment based on the one or more abnormalities. The method may comprise designing a treatment based on the one or more abnormalities. The method may comprise modifying a treatment based on the one or more abnormalities.

The one or more abnormalities may be in a bone. The one or more abnormalities may comprise fracture-vulnerable bone. The treatment may comprise an anabolic therapy or other bone active intervention.

According to a second broad aspect of the invention, there is provided a computer-implemented method for identifying abnormality in one or more measurements, comprising: receiving or accessing at least one first dataset comprising measurements of a normal population or sample and at least one second dataset comprising measurements of an abnormal population or sample; generating an image or map by imagizing the datasets (such as by imagizing the datasets comprises converting geometric virtual coordinates representative of a dataset into an image resulting in a cloud of points representative of normal or abnormal subjects); identifying a normality zone within the image using the first dataset; identifying an abnormality zone within the image using the second dataset; determining a definition of abnormality based on a comparison of the normality zone and the abnormality zone; receiving or accessing at least one third dataset comprising measurements of an unknown population or sample; and determining from the definition of abnormality which of the one or more measurements correspond to abnormality. The measurements of the normal population or sample and the measurements of the abnormal population comprise co-measurements.

Determining a definition of abnormality may include defining normality. The measurements may comprise twoor more dimensional ordered pairs of co-measurements (of either co-dependent or non co-dependent parameters).

According to a third broad aspect of the invention, there is provided a computer-implemented method for building a software device that can be used to define and quantifying abnormality of a measurement. The device can also (such as in a default mode) define and quantify the extent of abnormality of a measurement.

The method of this aspect comprises: receiving or accessing at least one first dataset comprising measurements of a normal population or sample and at least one second dataset comprising measurements of an abnormal population or sample; generating an image or map by imagizing the datasets (such as by imagizing the dataset comprises converting geometric virtual coordinates representative of a dataset into an image resulting in a cloud of points representative of normal or abnormal subjects); identifying a normality zone within the image using the first dataset; identifying an abnormality zone within the image using the second dataset; determining a definition of abnormality based on a comparison of the normality zone and the abnormality zone; and outputting a software device adapted to define and quantify the extent of abnormality of measurements in one or more other datasets. The measurements of the normal population or sample and the measurements of the abnormal population comprise co-measurements.

In an embodiment, the method comprises obtaining the measurements of the normal population or sample by measuring one or more normal samples or subjects, and obtaining the measurements of the abnormal population or sample by measuring one or more abnormal samples or subjects.

The device (or 'abnormality quantifier') may be in the form of a discrete software application (e.g. downloadable to a computing device), a software program, a webpage, or any calculator. The device, once self-trained, can also be used to define and quantify the extent of abnormalities in other datasets.

The device or abnormality quantifier may be in the form of a computing device, or a discrete software application (e.g. downloadable to a computing device), a software program, a webpage, or any calculator; in a form of an imaging device such as a computed tomography (CT), a magnetic resonance machine (MRI), a blood test device such as a coulter count, a urine or saliva analysis device or an ultrasound. The device, once self-trained, can also be used to define and quantify the extent of abnormalities in other datasets.

Hence, according to a fourth broad aspect of the invention, there is provided a computer-implemented method for identifying abnormality in one or more measurements (such as of subjects or members of a cohort), comprising: receiving or accessing at least one first dataset comprising measurements of a normal population or sample; receiving or accessing a definition of abnormality generated according to the method of the first or second aspect of the invention; and determining from the definition of abnormality which of the one or more measurements correspond to abnormality.

Each method of these aspects may include the following features.

For example, the method may include binarizing the imagized dataset using an image binarizer before identifying the zones.

In an embodiment, determining the normality zone comprises segmenting the spatial zone corresponding to the imagized normal dataset (using any suitable spatial segmentation technique).

In an embodiment, the abnormality zone comprises segmenting the spatial zone corresponding to the imagized abnormal dataset (using any suitable spatial segmentation technique).

In one embodiment, the method comprises segmenting the normality and abnormality zones using a threshold based segmentation method or an edge detection segmentation method.

In another embodiment, the method comprises segmenting the normality and abnormality zones using density-based spatial clustering of applications with noise (DBSCAN).

In another embodiment, the method comprises segmenting the normality or abnormality zones using a density profile analysis, such as that disclosed in international patent application publication no. WO 2011/029153.

In this embodiment, points corresponding to the zone are treated as a first material and points not occupied are treated as a second material. The method then comprises segmenting the normality zone using an approach comparable to that disclosed in WO 2011/029153. This comprises (i) identifying all the 'rough' or external contours of the zone (normal or abnormal), that is, using all normal or abnormal points respectively within the image;

(ii) from the rough contouring, defining automatically a plurality of regions of interest within the image, each of the regions of interest having a width of one or more points (pixels or voxels);

(iii) determining respective density, intensity or attenuation profiles within the regions of interest;

(iv) determining a location of the junction including defining a first reference point within one of the first and second materials and employing the first reference point as current reference point;

(v) determining a closest point to the current reference point that is on the respective profile and in the other of the first and second materials to that of the current reference point;

(vi) locating a greatest difference in values of the respective profile between an adjacent peak and trough in a segment of the respective profile between the current reference point and the closest point;

(vii) locating a point of inflexion in the segment;

(viii) using the line corresponding to the point of inflexion (x-value) as a new referent point;

(ix) using the new referent point to identify the external edge of the zone in the analysed region of interest;

(x) repeating steps (i) to (ix) after rotating the selected region of interest 360° around each of the proposed reference points at the external edge in turn;

(xi) merging all the analysed regions of interest to identify the external edges of position of the normality or abnormality zone between measurement (A) and measurement (B).

The method may comprise defining and quantifying the extent of normality by a normality definer.

The method may comprise defining and quantifying the extent abnormality by an abnormality definer.

In one embodiment, the normality definer defines normality using the spatial characteristics of the normal zone, such as the external edges and the most central point in the zone. The central point is the most representative of normality, defined by any suitable criterion; in this embodiment, it may be the centroid, a geometric center, or a point with coordinates being the average values of both the measurement and the co-measurement. The choice of the most central value highlight the intent to capture the most normal value in the normality zone (most normal point).

In one embodiment, abnormality definer defines abnormality using the spatial characteristics of the abnormal zone such as its shape in relation to that of the normal zone.

In an embodiment, an abnormality definer defines abnormality using a linear exit vector with an origin being the most normal point as determined by a normality definer and a direction being that of the sum of the vectors extending from the most normal point to the respective points in the abnormal zone corresponding to the abnormal dataset (which may or may not be in a zone overlapping with the normal zone).

In another embodiment, an abnormality definer may define and quantify abnormality using a path rather than a linear exit vector. A path may be defined as a series of consecutive vectors the first originating in any point in the normal zone, and the end of the vector being points in the nearest sub-zone of the abnormal zone and corresponding to the abnormal dataset (they may or may not be in a zone overlapping with the normal zone). The subsequent vector has its origin where the first vector ended and ends in the near sub-zone in the abnormality until all sub-zones of the abnormality zone have been covered.

According to one aspect, the invention provides a method in which abnormality is defined according to a spatial position—which may be expressed as an angular direction (from 0 to 360°, for example) about a centre of normality—of the abnormal points or of the main concentration of the abnormal points. That is, points of the abnormal dataset, which should be predominantly outside the normality zone, may be spatially positioned at any angle in a frame of reference with an origin at the most central point of normality and coordinates similar to those of the centre of normality or most normal point.

For example, for a particular condition of abnormality (which may relate to a particular disease), the abnormal points may be predominantly at and around −45°; in other conditions of abnormality they may be around +45° or −90° or otherwise. The exit vector described above identifies or coincides with this direction of abnormality.

This spatial direction of abnormality may thus be identified using, for example, the shape of the abnormality zone, an exit vector, or an exit path starting in the normality zone (such as at the most normal point).

A method in which a maximum abnormality is defines as the point further away from the normal point as identified by the normality identifier (e.g., mid point or centroid) and the spatial direction in which abnormality occurs as identified by abnormality identifier.

A method in which the magnitude of abnormality is quantified by the abnormality quantifier is as a function of their spatial position relative to the identified maximum abnormality. This may be in a square area, a rectangular area, a triangular area or an elliptical area near the maximum disease point.

In one embodiment, abnormality is quantified as a distance from the identified maximum abnormality. In another embodiment, the method comprises treating abnormality as a weighted distance from a maximum abnormality. In another embodiment, the method comprises quantifying abnormality as a weighted distance from maximum abnormality and deviation from the exit path or exit path.

The method may comprise optimizing the results of abnormality identifier by testing the performance of the identified abnormal values.

The method may comprise controlling the normality identifier to modify characteristics used to identify normality (e.g., most normal point, edges, etc) and/or controlling the abnormality definer to modify characteristics used to identify abnormalities (e.g. shape, linear vector, exit path, etc).

The method may comprise re-testing performance of the characterization of abnormality determined according to this method in identifying abnormal values until suitable performance has been reached. The suitable performance may be a preset value.

The method may comprise the abnormality definer defining abnormality in another set of two or more co-measurements.

Merging the results between two or more optimized results may include defining as abnormal a subject that has a measurement appearing to be abnormal in at least one matrix (representing a co-measurement), represented by two or more imagized datasets, or defining as abnormal a subject that has a measurement appearing to be abnormal in most matrices (representing a co-measurement), represented by two or more imagized datasets.

In one embodiment, the abnormality quantifier builder may be set so that all normal co-measurements occupy a predefined scale (e.g., 0 to 100). In this embodiment, the maximum abnormal (or disease point) is set as 0 regardless of the abnormality. Thus, this provides a universal definition of abnormality.

The abnormality quantifier builder then outputs an 'abnormality quantifier'. In one embodiment this abnormality quantifier is embodied as software.

In other embodiment, the abnormality quantifier is embodied as a discrete software application, is provided via a webpage that quantifies specific abnormality, or any other calculator.

In another embodiment, the abnormality quantifier is set output define and quantify the extent of abnormality for the measurement it has self-trained itself.

According to a further broad aspects, the invention provides apparatuses configured to implement any of the methods described above.

For example, in one aspect, the invention provides an apparatus for identifying abnormality in one or more measurements (such as of subjects or members of a cohort), the apparatus comprising: a processor; a memory; a data imagizer configured to generate an image or map by imagizing at least a first and a second dataset (such as by imagizing the datasets comprises converting geometric virtual coordinates representative of a dataset into an image resulting in a cloud of points representative of normal or abnormal subjects); a zone identifier configured to identify a normality zone within the image using the first dataset and identify an abnormality zone within the image using the second dataset; an abnormality definer configured to determine a definition of abnormality based on a comparison of the normality zone and the abnormality zone; and an outputter for outputting at least one result. The first and a second datasets comprise co-measurements.

Imagizing the first and second datasets may comprise converting geometric virtual coordinates representative of a dataset into an image resulting in a cloud of points representative of normal or abnormal subjects.

The apparatus may include a normality definer configured to determine a definition of normality. The apparatus may include a binarizer.

According to a further broad aspect, the invention provides executable instructions or software (such as embodied in a computer readable medium, for example with the executable instructions or software imbedded or permanently stored therein), that, when executed by a computing device or processor of a computing device, cause the computer or processor to perform any of the methods of the above aspects.

The result of the analysing step would generally be outputted so that it can be used to define normal versus abnormal, but may be outputted to a memory or memory medium for later used.

According to another broad aspect, the invention provides a computing device provided with executable instructions or software that, when executed by the computing device or by a processor of the computing device, cause the computing device or processor of the computing device to perform any of the methods of the above aspects.

It should be noted that any of the various individual features of each of the above aspects of the invention, and any of the various individual features of the embodiments described herein including in the claims, can be combined as suitable and desired.

BRIEF DESCRIPTION OF THE DRAWING

In order that the invention may be more clearly ascertained, embodiments will now be described, by way of example, with reference to the accompanying drawing, in which.

DETAILED DESCRIPTION

Figure 1:
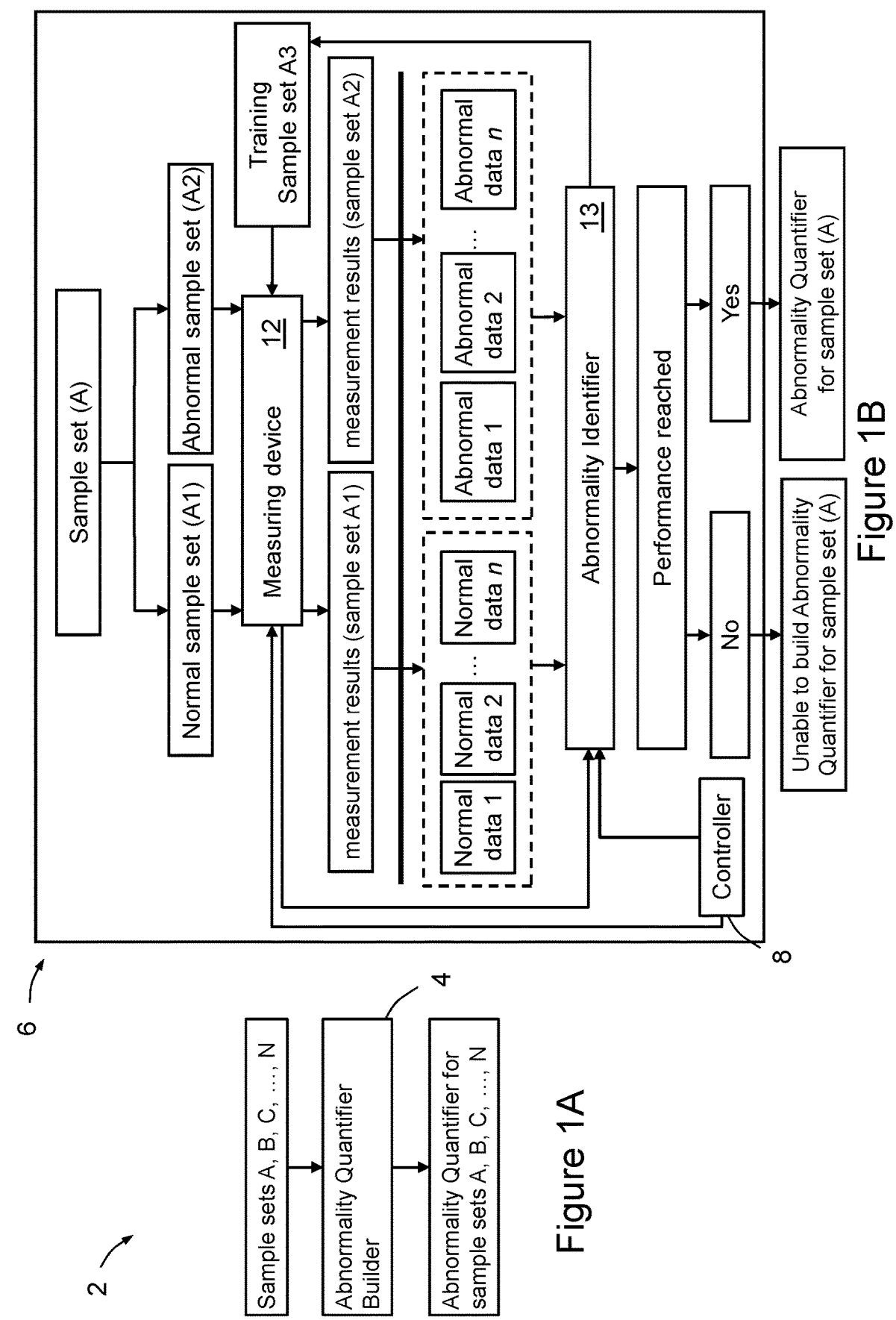
FIG. 1A is a schematic view of an abnormality quantifier builder according to an embodiment of the present invention.
FIG. 1B is a schematic representation of the operation of the abnormality quantifier builder of FIG. 1A in building an abnormality quantifier.
Figure 2:
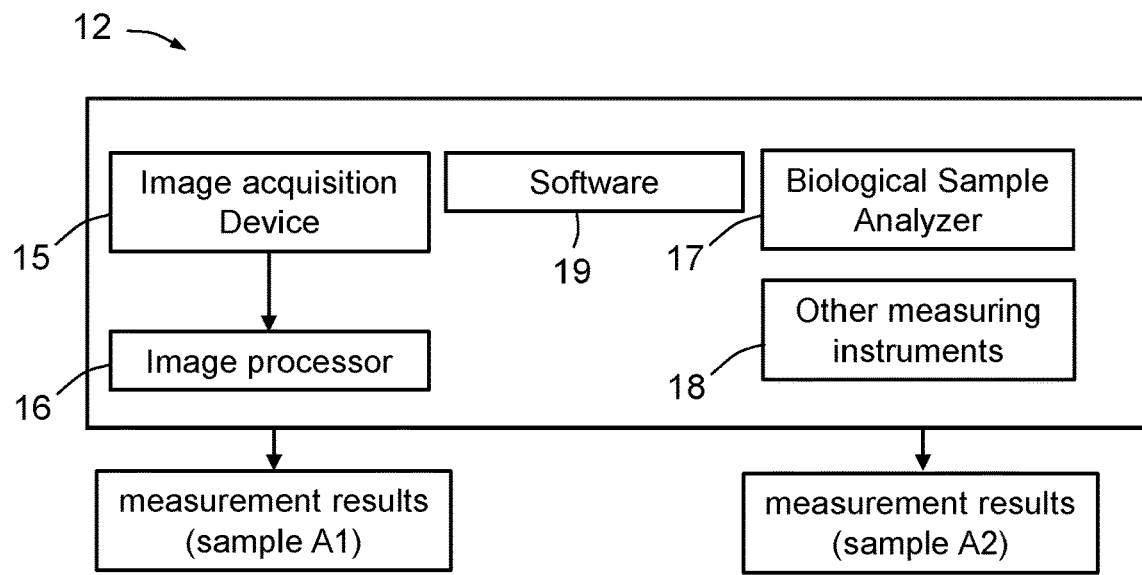
FIG. 2 is a schematic view of the measuring device of the abnormality quantifier builder of FIG. 1A.

An abnormality quantifier builder 4 according to an embodiment of the present invention operates as shown schematically at 2 in FIG. 1A, while FIG. 1B is a more detailed schematic representation 6 of the operation of abnormality quantifier builder 4 in building an abnormality quantifier. Broadly speaking, samples sets A, B, C, . . . , N are uploaded into abnormality quantifier builder 4, which then builds an abnormality identifier for those sample sets. The outputted abnormality quantifier is designed to quantify abnormalities in one or more sample sets.

Referring to FIG. 1B, abnormality quantifier builder 4 operates as follows. Sample Set A may relate, for example, to an individual, an anatomical part of the individual such as a bone, heart, brain, kidney, or a biological sample such as saliva, blood or urine. The sample may also be a non-biological material such as a rock. The sample set may also be comprise an image or images of any of the aforementioned materials.

Abnormality quantifier builder 4 divides the sample set into two populations: a first population of normal samples ('sample set A1') and a second population of abnormal samples ('sample set A2'). Sample set A1 is free of abnormality, but sample set A2 may have many types of abnormalities. Abnormality quantifier builder 4 builds an abnormality quantifier that can quantify the specific abnormality existing in sample set A.

Controller 8 of abnormality quantifier builder 4 controls a measuring device 12 of abnormality quantifier builder 4 to output selected set(s) of measurement results for both normal and abnormal samples sets A1, A2. These measurement results sets are selected based on the likely ability to distinguish normal versus abnormal for a specified abnormality. For example, the set of measurement results may be of cortical bone porosity and trabecular bone density if the abnormality is fracture-vulnerable bone, or height and weight if the abnormality is obesity.

Abnormality quantifier builder 4 may also be preset to build the abnormality quantifier for one or more specific sample(s) and for specific abnormalities in that or those samples. In that case, abnormality quantifier builder 4 automatically recognises the sample set and performs the specific desired measurements without the input of controller 8.

The measurement results are then uploaded (typically automatically) into an abnormality identifier 13 of abnormality quantifier builder 4. In other circumstances, controller 8 may upload the measurement results into abnormality identifier 13 if the measurement results were performed by a measuring device other than measuring device 12 of abnormality quantifier builder 4.

Abnormality identifier 13 then processes the sets of normal and abnormal measurements, and defines the abnormality. Next, abnormality quantifier builder 4 requests a third population of samples (sample set A3). Sample set A3 is the testing population. It contains both known normal and abnormal examples of the type of sample set A. Measuring device 12 measures and provide the preselected measurements likely to distinguish normal and abnormal samples to the built abnormality quantifier. The abnormality quantifier tests and modifies its own performance. If the desired performance cannot be reached, then abnormality quantifier builder 4 outputs to controller 8 that an acceptable abnormality quantifier could not be built for the sample set and abnormality, at the desired performance level. If the desired performance is reached then abnormality quantifier builder 4 outputs the abnormality quantifier for sample set A and the specific abnormality FIG. 3A is a schematic view of measuring device 12. measuring device 12 includes an image acquisition device 15, an image processor 16, a biological sample analyzer 17, one or more other measuring instruments 18, and controlling software 19.

Figure 3A:
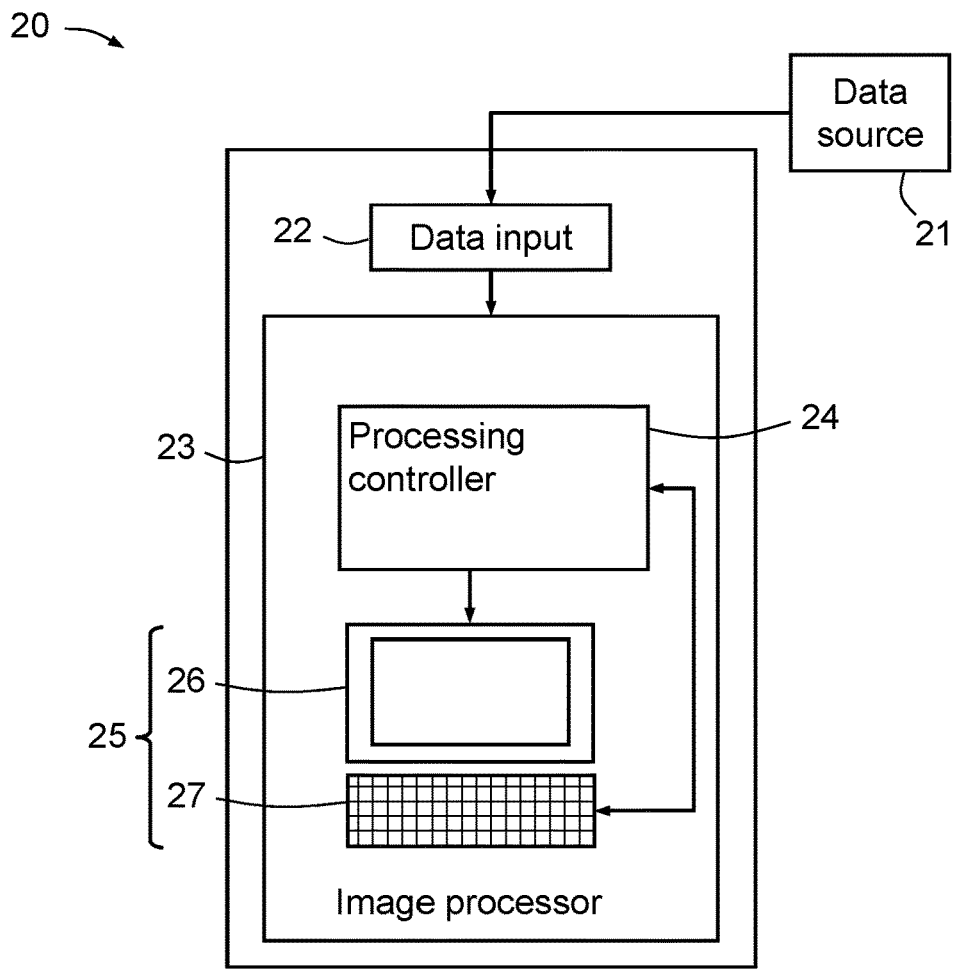
FIG. 3A is a schematic view of a system for identifying and quantifying abnormal values according to an embodiment of the present invention.

A system for identifying and quantifying abnormality (which may be referred to as an abnormality identifier), built by abnormality quantifier builder 4, according to an embodiment of the present invention, is shown schematically at 20 in FIG. 3A, shown with a data source 21. System 20 includes a data input 22 and an image processor 23. Image processor 23 includes a processing controller 24; processing controller 24 includes several components, which are described below. Image processor 23 also includes a user interface 25. User interface 25 comprises, in this example, a display 26 and a keyboard 27, but it will be appreciated that other known user interfaces or combinations thereof may be employed, including a computer mouse, a touch screen, a scanner, a printer and another computing device.

The data source 21 may comprise, for example, a data collection/creation device (such as CT scanner with data analysis capacity), a database, computer readable data medium, a computing device with user interface, or a network connection to any of these.

Figure 3B:
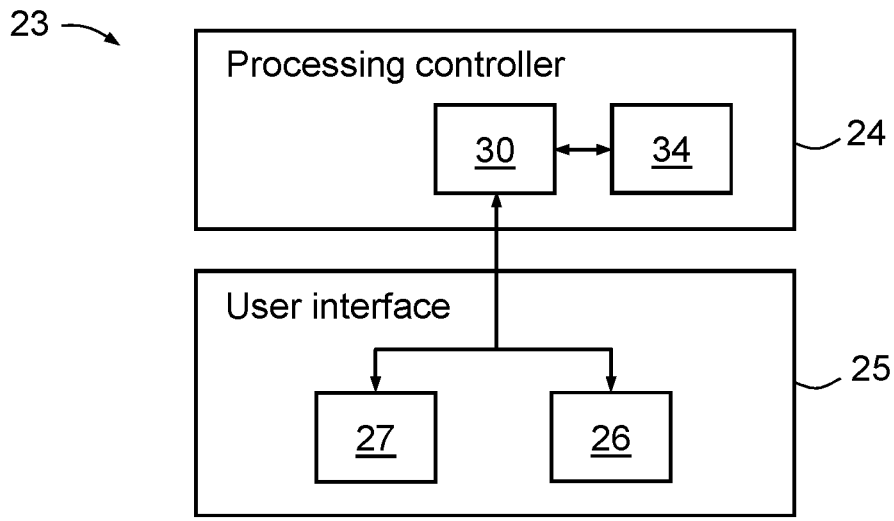
FIG. 3B is a more detailed schematic view of the system of FIG. 3A according to an embodiment of the present invention.
Figure 3C:
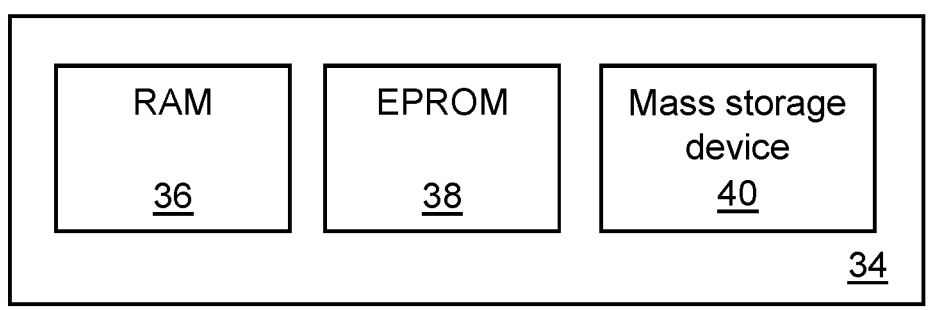
FIG. 3C is a schematic view of the memory of the processing controller of the image processor of the system of FIG. 3A according to an embodiment of the present invention.

FIGS. 3B and 3C are more detailed schematic view of components of system 10. Referring to FIG. 3B, processing controller 24 includes a processor 30 and a memory 34 in data communication with each other. Referring to FIG. 3C, memory 34 includes RAM 36, EPROM 38 and a mass storage device 40. An instruction set may be stored in mass storage device 40 and, when required, loaded into RAM 36 for execution by processor 30. The instruction set is adapted to control system 10 to perform the steps of the method of this embodiment, as described below.

Data input 22 is adapted to receive datasets from data source 21. These datasets include, as is described in greater detail below, one or more datasets of normal values (that is, data correspond to a cohort or cohorts of normal subjects) and one or more datasets of abnormal values (that is, data correspond to a cohort or cohorts of abnormal subjects). Each dataset comprises, in this example, two-dimensional data points, that is, comprising ordered pairs of values. These values relate to respective physical characteristics of the subjects. It will be appreciated that data of other dimensionality (whether one-, three- or higher) may be employed, each comprising one, three or more values respectively that relate to respective characteristics of the subjects. In this example, in which each data point comprises an ordered pair of values, the first value may be referred to as "the measurement" and second value as the "co-measurement", or the first may be referred to as "measure A" and the second as "measurement B". If, for example, a dataset comprised values for the measurement of the height and weight (such as when the abnormality is obesity) of a cohort of subjects, one might refer to the height as the measurement and the weight as the co-measurement, or vice versa; or one might refer to the measurement of height as measurement A and the measurement of weight as measurement B, or vice versa.

This terminology is not intended to suggest, however, that there is necessarily a correlation between the measurement and the co-measurement (or measurements A and B). In some contexts, the term "co-measurement" refers to a set of ordered pairs (or triplets, etc) of measurements, but this will be apparent from the context.

Figure 5:
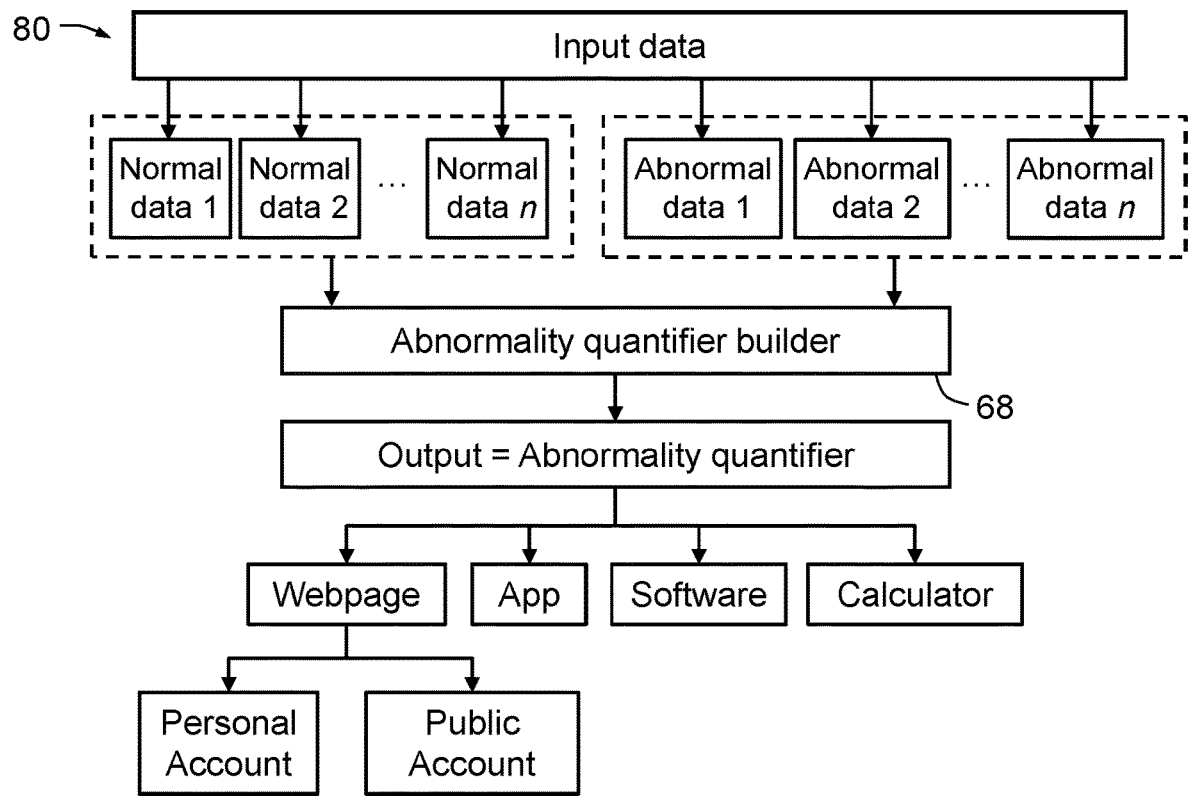
FIG. 5 is a schematic view of the operation of the processing controller of the abnormality quantifier builder of the system of FIG. 3A according to an embodiment of the present invention.

These data may be uploaded into an abnormality quantifier builder (see FIG. 5) which builds an abnormality quantifier, which is outputted in a form a webpage, a discrete software application, software, or any form of calculator. The abnormality quantifier may also output results as quantified measured of abnormality rather than an abnormality quantifier device.

Figure 4:
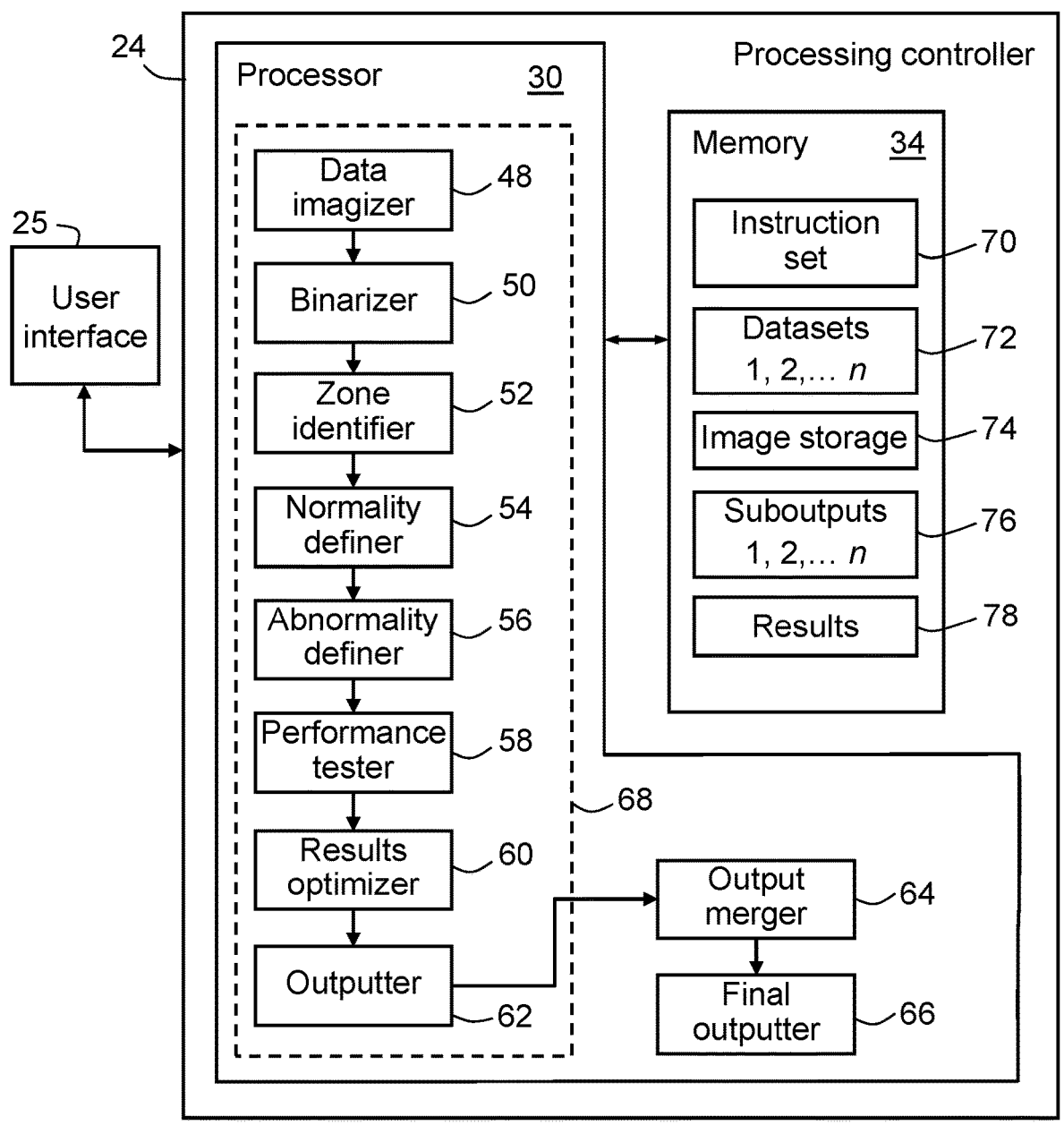
FIG. 4 is a schematic view of the processing controller of the image processor of the system of FIG. 3A according to an embodiment of the present invention.

FIG. 4 is a schematic view of processing controller 24 of image processor 23, together with user interface 25. Processing controller 24 includes processor 30 and memory 34. Processor 30 includes a data imagizer 48, a binarizer 50, a zone identifier 52, a normality definer 54, an abnormality definer 56, a performance tester 58, a results optimizer 60, an outputter 62, an output merger 64 and a final outputter 66.

Data imagizer 48, binarizer 50, zone identifier 52, normality definer 54, abnormality definer 56, performance tester 58, results optimizer 60 and outputter 62 may also be provided as or constitute an abnormality quantifier builder 68, the characteristics and operation of which are described below. It should be noted, however, that abnormality quantifier builder 68 is also configured to build a software device based on exemplary datasets known to be derived from, respectively, normal and abnormal populations, such that abnormality quantifier builder 68 can then be used with future datasets derived from like populations and determine which points in the future datasets are 'normal' and which are 'abnormal.'

Memory 34 includes the aforementioned instruction set 70, datasets storage 72 of datasets 1, 2, . . . , n (for storing respective datasets), image storage 74 (for storing images generated by data imagizer), suboutputs storage 76 (for storing suboutputs 1, 2, . . . , n), and results storage 78.

Data imagizer 48 is adapted to transform the normal and abnormal values into an image or map (which, in this context may be regarded as synonymous). This process may be referred to as imagization of the datasets. Data imagizer 48 can then control system 10 to output the resulting image or map (see, for example, those illustrated in FIGS. 7A to 7D and 8), such as to display 26 for inspection by a user, but it should be appreciated that it is not essential that the image or map be outputted.

The process of imagization by data imagizer 48 may optionally involve binarization. Binarization aims to facilitate image processing (including the identification of zones within the image) with minimal deleterious effect on accuracy. Any suitable binarization technique may be employed.

The image, once binarized, is processed to identify normal and abnormal the zones as follows. All points in the normal and abnormal sets of data are respectively given the same value resulting in an image where points belonging to the proposed population (normal or abnormal) are foreground and those not belonging to any dataset are background.

After the dataset has been imagized (and optionally binarized), then zone identifier 52 processes the images (i.e. imagized dataset) to identify the normal and abnormal zones corresponding respectively to the zone produced by the dataset of normal data and the zone produced by the dataset of abnormal data.

It should be noted that the image does not need to be viewed in order for zone identifier 52 to identify normality and abnormality zones of the image.

In one embodiment, zone identifier 52 uses the 'density-based spatial clustering of applications with noise' (DBSCAN) technique. This technique groups together points that are closely packed, marking points that lie alone in low-density regions as outliers. The algorithm classifies a set of points into three types: core points, density reachable points and outliers, as follows:

i) A neighbourhood of a point p is the range within distance r of it. A point p is a core point if there are at lease m points in its neighbourhood. Those points are said to be directly reachable from p. No points are directly reachable from a non-core point.

ii) A point q is reachable from p is there is a path $p_1, \ldots, p_n$ with $p_1=p$ and $p_n=q$, where each $p_{i+1}$ is directly reachable from $p_1$.

iii) All points not reachable from any other point are determined to be outliers.

However, in the present embodiment, zone identifier 52 uses the image processing technique disclosed in WO 2011/029153. This technique includes:

(i) identifying all the 'rough' or external contours of the zone (normal or abnormal), that is, using all normal or abnormal points respectively within the image;

(ii) from the rough contouring, defining automatically a plurality of regions of interest within the image, each of the regions of interest having a width of one or more points (pixels or voxels);

(iii) determining respective density, intensity or attenuation profiles within the regions of interest;

(iv) determining a location of the junction including defining a first reference point within one of the first and second materials and employing the first reference point as current reference point;

(v) determining a closest point to the current reference point that is on the respective profile and in the other of the first and second materials to that of the current reference point;

(vi) locating a greatest difference in values of the respective profile between an adjacent peak and trough in a segment of the respective profile between the current reference point and the closest point;

(vii) locating a point of inflexion in the segment;

(viii) using the line corresponding to the point of inflexion (x-value) as a new referent point;

(ix) using the new referent point to identify the external edge of the zone in the analysed region of interest;

(x) repeating steps (i) to (ix) after rotating the selected region of interest 360° around each of the proposed reference points at the external edge in turn;

(xi) merging all the analysed regions of interest to identify the external edges of position of the normality or abnormality zone between measurement (A) and measurement (B).

According to this embodiment, after zone identifier 52 has defined the normality or abnormality zones by segmentation of the imagized dataset, normality definer 54 and abnormality definer 56 define normality and abnormality, and abnormality definer 56 quantifies the extent of abnormality.

In this embodiment, normality definer 54 defines normality using the spatial geometry of the segmented normal zone.

To define normality, normality definer 54 may do so in terms of the external edge or the most central point in the normality zone. The most central point may be the centroid, or a point with coordinates that are the average values of both the measurement and the co-measurement. Abnormality quantifier builder 68 chooses the most central point to ensure that it captures the most normal value in the normality zone (i.e. the 'most normal point').

After normality definer 54 has defined normality, abnormality definer 56 uses the defined values of normality and the characteristics of the abnormality zone to define abnormality. The characteristics of the abnormality zone used to define abnormality may comprise the shape, in particular the shape in relation to that of the normality zone. By default, in this embodiment, abnormality definer 56 employs the exit vector defined as the direction of abnormality (e.g., "−45°", such as is approximately the case in—for instance—FIG. 7A) as the abnormality quantifier.

The shape of the abnormality zone and its orientation relative to those characteristics of the normality zone (e.g., the most normal point such as the centroid) may be used to define abnormality. The spatial orientation of the abnormality zone may be used to define abnormality because points exiting the normality zone may exit at any point of the perimeter of the normality zone.

To determine the spatial orientation of abnormality, abnormality definer 56 may ascertain that the abnormality zone has a generally elliptical shape or may fairly be characterized with an ellipse, so the major axis of the ellipse originating from the normal zone's most normal (viz. representative) point may be used to characterize the abnormality zone's spatial orientation.

Abnormality definer 56 may ascertain that the abnormality zone has other shapes, but in each case that shape and its orientation can serve to characterize the abnormality zone and its spatial orientation.

In this embodiment, abnormality definer 56 defines abnormality using a linear exit vector with an origin being the most normal point as determined by normality definer 54 and a direction being that of the sum of the vectors extending from the most normal point to the respective points in the abnormal zone corresponding to the abnormal dataset (which may or may not be in a zone overlapping with the normal zone).

In other embodiment, abnormality definer 56 may define and quantify abnormality using a path rather than a linear exit vector. A path may be defined as a series of consecutive vectors the first originating in any point in the normal zone, and the end of the vector being points in the nearest sub-zone of the abnormal zone and corresponding to the abnormal dataset (they may or may not be in a zone overlapping with the normal zone).

The subsequent vector has its origin where the first vector ended and ends in the near sub-zone in the abnormality until all sub-zones of the abnormality zone have been covered.

Abnormality definer 56 may define abnormality by other techniques as desired, but regardless of the method employed by abnormality definer 56 to define abnormality, abnormality definer 56 then uses the direction of abnormality to find the point maximum abnormality.

In this embodiment, maximum abnormality is defined as the point furthest away from the normal point as identified by normality identifier 54 in the direction that was defined as the direction of abnormality by the abnormality definer 56. The normality point may be a point corresponding to the average values of both co-measurements.

After identifying the point of maximum abnormality, abnormality definer 56 quantifies the magnitude of abnormality as a function of spatial position relative to the identified maximum abnormality. This may be a square area, rectangular area, triangular area, or elliptical area near the maximum abnormality point.

In another embodiment, abnormality definer 56 may quantify abnormality as a distance from the identified maximum abnormality. In still another embodiment, abnormality definer 56 may quantify abnormality as a weighted distance from maximum abnormality, or as a weighted distance from maximum abnormality and deviation of the exit vector or exit path. For example, there is an exit vector (say, −45°), the further away an exit point is from this optimal exit angle, the less likely it is to be abnormal.

Next, results optimizer 60 optimizes the results of abnormality identifier 56 by testing the performance of the identified abnormal values. Abnormality identifier 56 provides the results to results optimizer 60, which then determines if the results are acceptable or not. A preset value of the minimal acceptable performance of abnormality identifier 56 may be employed. For example, the preset value may be 70%, meaning that abnormality identifier 56 must be found to correctly identify as abnormal 70% of abnormal points to be deemed to satisfactory.

To optimize the results, results optimizer 60 tests the performance of the results. This may be done using any suitable test of performance of the output of a measurement, such as receiver operating characteristic (ROC), or ROC curve, an odd ratio or any other form of performance evaluation test.

Abnormality quantifier builder 68 may have a preset performance threshold. If this has been reached then, abnormality quantifier builder 68 can be controlled to output a device ready to define abnormality between the measurements and co-measurements.

If the preset performance threshold has not been reached, results optimizer 60 may improve the results by controlling the normality definer 54 to modify the characteristics used to identify normality (e.g., most normal point, edges, etc) and/or control abnormality definer 56 to modify the characteristics used to identify abnormalities (e.g., shape, linear vector, exit path, etc).

When this is done, performance tester 58 again tests the performance of abnormality definer 56. This may include testing against a preset normality value. The process may be repeated a predetermined number of times (e.g. 10 times). When all the possible preset options (e.g., shapes ranging from circle to an ellipse with minor-axis≅0) have been examined, results optimizer 60 provides the results of the co-measurements to outputter 62.

Outputter 62 assesses whether other datasets require processing. If not, outputter 62 outputs the results; if so, the sets of other datasets are analysed—that is, processing returns to data imagizer 48 where processing commences of the next dataset (which may relate to a different abnormal condition or to a further set of measurements of an earlier dataset).

After all co-measurements have been analysed, output merger 64 merges the results of abnormality. Output merger 64 may merge the results of abnormality according to, for example, any of these criteria:

measurements appearing as abnormal in at least one matrix (representing a co-measurement), represented by two more imagized datasets;

measurements that appear as abnormal in most such matrices; and/or measurement that appear as abnormal is the fewest of such matrices.

Figure 6:
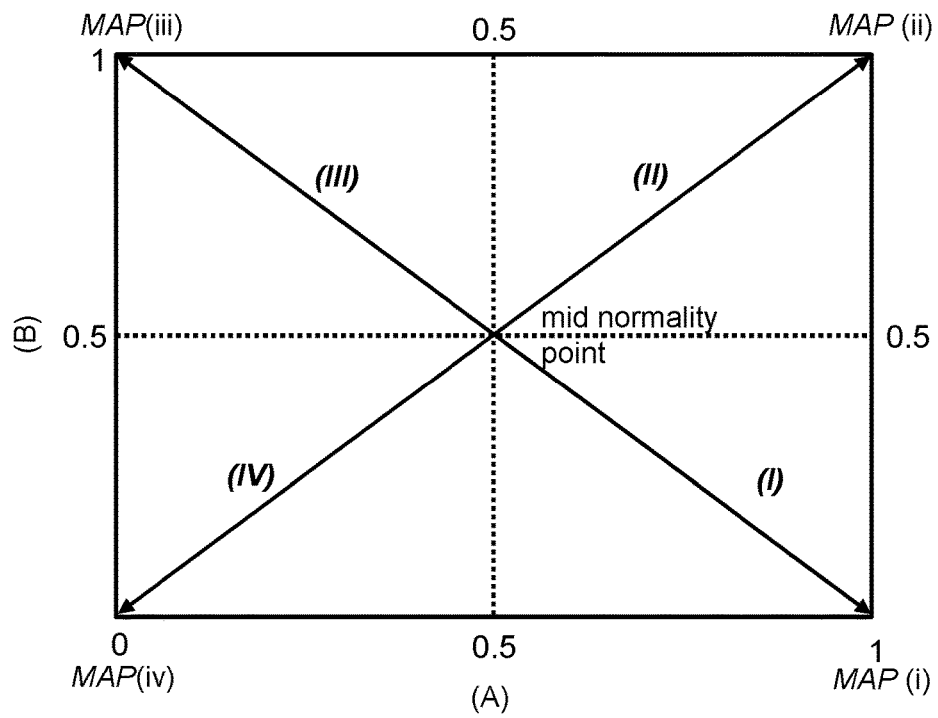
FIG. 6 schematically illustrates the manner in which measurements can be rendered unitless in the application of the system of FIG. 3A according to an embodiment of the present invention.

Referring to FIG. 6, in one embodiment, abnormality quantifier builder 68 may be configured such that all normal measurements (A, B) are in a predetermined scale (e.g., 0 to 100), so effectively unitless. In this example, the maximum abnormal point (which may correspond to a disease point) is set as 0 regardless of the abnormality. Thus, this provides a universal definition of abnormality. FIG. 6 depicts this concept schematically.

Abnormality quantifier builder 68 then outputs an 'abnormality quantifier'. In one embodiment an 'abnormality quantifier' is software. In another embodiment, the abnormality quantifier is a discrete software application, a webpage that quantifies specific abnormality, or any other suitable calculator. In still another embodiment, the abnormality quantifier is an imaging device, a device that analyses a biological sample, or an ultrasound device.

In another embodiment, the abnormality quantifier defines and quantifies the extent of abnormality for the measurement it has self-trained itself to quantify.

In one embodiment, the abnormality quantifier is a medical device such as an imaging device with the measuring device being a computed tomography (CT) scanner with an in-built image processing software. In another embodiment, the abnormality quantifier is a medical device with a measuring device in the form of an image processing device. The image processing device may use any suitable image processing technique (such as that disclosed in international patent application publication no. WO 2011/029153). In another embodiment, the medical device is an analyser of biological samples, such as an assay. The medical device may identify abnormalities such as those produced by diseases or normal physiological processes such as ageing or physical exercise. In these circumstances, the medical device may be used as an aid in the diagnosis of disease in an individual. The medical device may quantify the changes in the extent of abnormality such that produced by treatments or influential factors such as lifestyle factors (smoking, alcohol consumption, physical exercise, etc). In these circumstances the medical device may be used as an aid in the monitoring of the effects of treatments or influential factors on an individual.

In the present description, the medical device built by the builder of abnormality quantifier is a device that identifies and quantifies the extent of abnormality in bone (see examples below). The abnormality may be a fracture-vulnerable bone and therefore requiring treatment to decrease the extent of abnormality in the bone. In these circumstances, repeated quantification of the extent of abnormality may be used to monitor the treatment. There are many treatments that many be used to do so, such as antiresorptives (e.g. an alendronate, denosumab, risedronate, selective estrogen receptor modulator (SERM) and odanacatib). The treatment may comprise an anabolic therapy, such as with teriparatide (intermittent parathyroid hormone), or Parathyroid hormone-related protein (PTH rp) such as abaloparatide or Humanized anti-sclerostin monoclonal antibody such as Romosozumab. Treatment may also entail modification of lifestyle factors such as physical exercise, diary food, calcium, and vitamin D intake.

According to a further embodiment, the invention provides executable instructions or software (such as embodied in a computer readable medium, for example with the executable instructions or software imbedded or permanently stored therein), that, when executed by a computer or processor of a computer, cause the computer or processor of the computer to perform the method for analysing a set of (optionally co-dependent) measurements as described above to output the extent of abnormality between two co-measurements or devices can be used to use to define and quantify the extent of abnormality between two co-measurements.

The result of the analysing step would generally be outputted so that it can be used to define normal versus abnormal, but may be outputted to a memory or memory medium for later used, may be outputted as a device (an application, software, a webpage, or any other calculator).

According to another embodiment, the invention provides a computing device provided with executable instructions or software that, when executed by the computing device or by a processor of the computing device, cause the computing device or processor of the computing device to perform the method for analysing of data of co-dependent variable as described above.

Thus, this embodiment attempts to address at least some of the problems arising from the shortcomings of some existing approaches. It takes into account the spatial position a data point to determine whether the specific point is normal or abnormal, and defines abnormality by a spatial direction where the point exit and the magnitude of the exit are defined as disease related, such that the magnitude of abnormality is related to the deviation from the expected position regardless of the absolute value.

EXAMPLES

Example 1

In this example, the sample was bone, and the abnormality was bone fragility (i.e., fracture-vulnerable bone) due to a reduced amount of bone or 'too little bone'—commonly referred to as osteoporosis.

Images of the bone were collected using a CT scanner. The measuring device of abnormality quantifier builder 4 was the image processor using the image processing technique disclosed in the international patent application publication no. WO 2011/029153. The processor had been preset to automatically output bone porosity (determined as a percentage) and trabecular density (determined in units of mgHA/cc) for the abnormality identifier. These measurements were preselected based on the assumption that, if the amount of bone is reduced, such a reduction would be apparent in both cortical and trabecular compartments. This makes these measurements likely to be good markers of bone fragility due to reduced amount of bone. If the assumption that these measurements are good markers of type of bone fragility is flawed or incorrect, then abnormality quantifier builder 4 would not be expected to build an abnormality quantifier for this type of bone abnormality; this is because any attempt to build an abnormality quantifier would be expected to fail to meet the acceptance criteria regardless of the level of optimization in defining abnormality by the abnormality quantifier. If this were to be the case, different parameters that were likely to be surrogates of a reduced amount of bone would need to be selected (or preselected) and used by abnormality quantifier builder 4 until an abnormality quantifier can be built. The selection or preselection of other likely parameters could be either automated or input by the controller as desired. However, if the assumption that bone porosity and trabecular density are good markers of bone fragility, the builder of abnormality quantifier will be able to build an abnormality quantifier for this type of bone fragility.

Figure 7A:
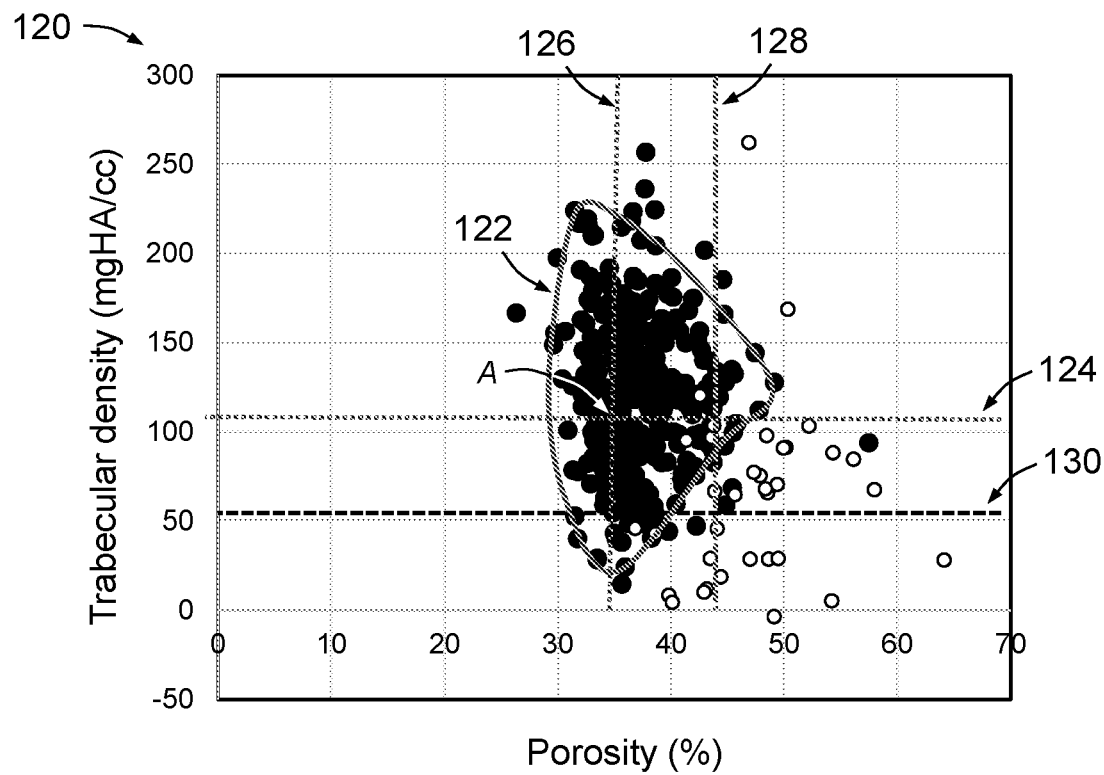
FIGS. 7A to 7D illustrate the analysis, by the system of FIG. 3A, of datasets comprising trabecular density and bone porosity values for a referent population of normal and abnormal subjects.

FIGS. 7A to 7D show examples of an image of datasets created by abnormality quantifier builder 4 from the measured values of porosity and trabecular density from a referent population and their analysis according to an embodiment of the present invention for determining normal and abnormal. FIG. 7A is an image 120 derived from datasets comprising trabecular density and bone porosity values for a referent population of normal and abnormal subjects.

In the figure, solid dots indicate normal subjects, and the normality zone is indicated by curve 122. 'Mid normality point' A was determined as the 'centre of mass' of all the normal points. Mid normality point A defines four quadrants in image 120, with boundaries defined by horizontal and vertical axes 124, 126 through mid normality point A.

Subjects with fractured bone due to documented reduced amount of bone, of which there are 35, are shown with hollow circles: the subjects may be described as diseased or 'abnormal.'

If the identification of abnormal subjects is based on high porosity alone (the threshold between normal and high porosity being indicated by dashed vertical line 128 at approximately 43.9%), 25 of the 35 abnormal subjects (only 71.4%) are identified as abnormal and 17 normal subjects would be identified as abnormal. This gives a positive predictive value of 17+25/52=59.5%.

If the identification of abnormal subjects were based on a thresholded low trabecular density alone of 5th percentile of young normal (indicated by horizontal dashed line 130), 13 of the 35 abnormal subjects (only 37.1%) would be identified as abnormal and 18 normal subjects would be identified as abnormal. This gives a positive predictive value of 13/(13+18)=41.9%.

By combining both of these tests in a thresholded manner, 32 of the 35 abnormal subjects (91.4%) are identified as abnormal but 35 normal subjects would be identified as abnormal, giving a low overall predictive value of 50%.

Figure 7B:
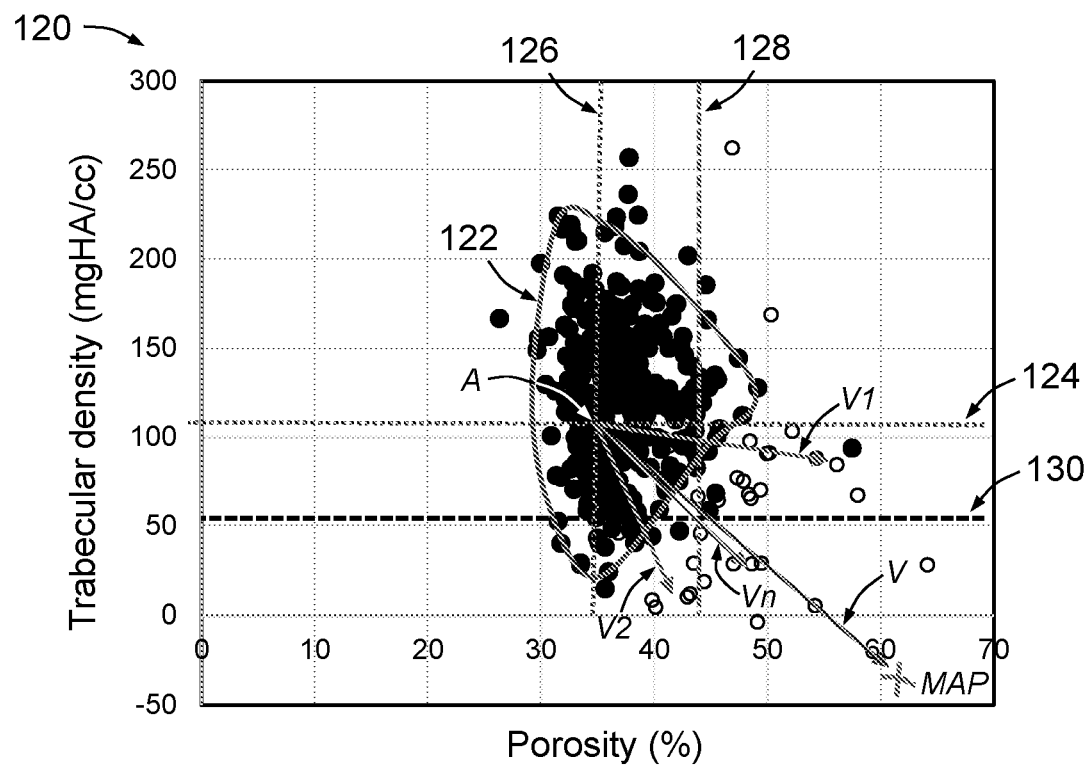
Figure 7C:
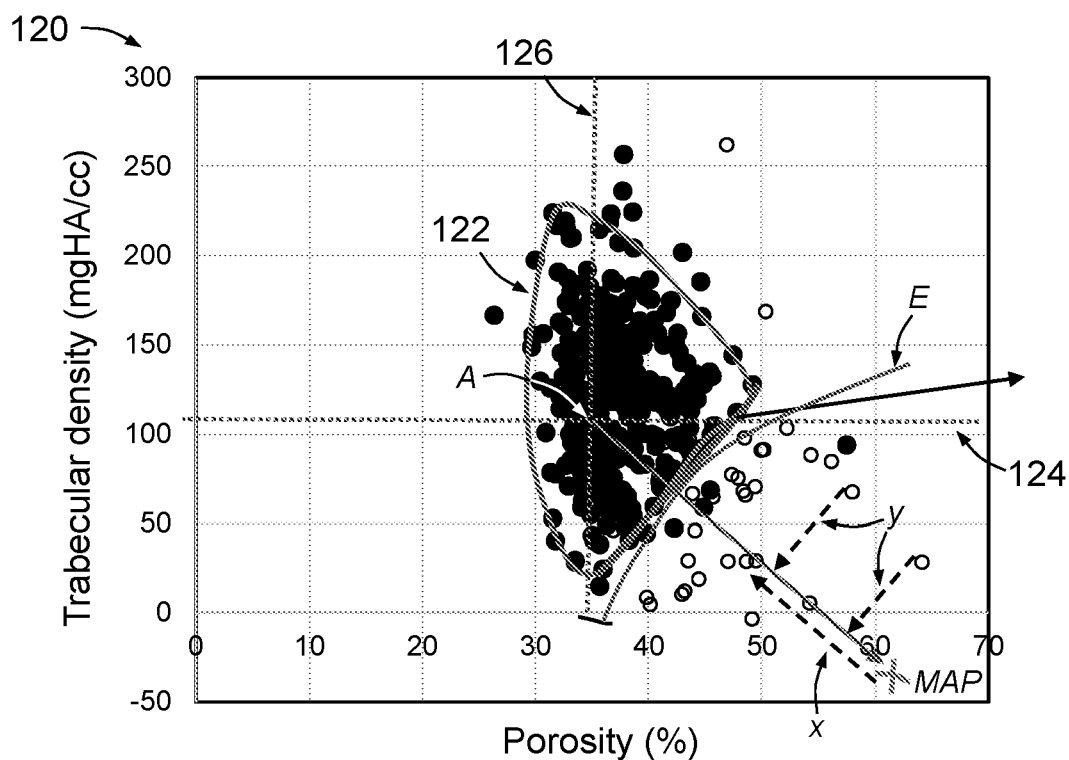
Figure 7D:
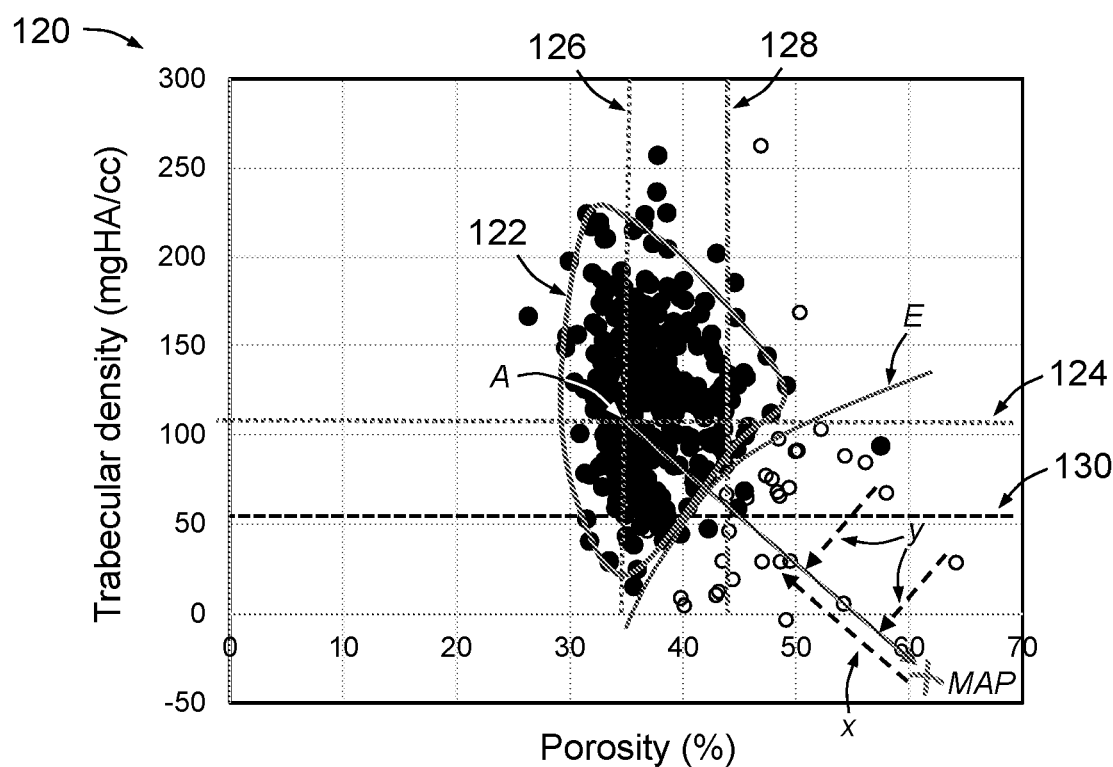

According to the present embodiment, the abnormality definer uses the point in image 120 that corresponds to the abnormality (that is, 'mid normality point' A) to find an exit (or abnormality) vector (V). Referring to FIG. 7B, vectors V1, V2, . . . , Vn are determined as the vectors from the mid normality point A to the respective abnormal points. Exit vector V is then determined as the sum of all the vectors V1, V2, . . . , Vn; that is, V=V1+V2+ . . . +Vn.

Abnormality definer then determines a maximum abnormal point (MAP), using the exit vector V. The maximum abnormal point is shown in the figure.

Abnormality may then be quantified based on the magnitude of the difference between the MAP and other points. Several approaches many be used.

In this embodiment, all points are projected onto the exit vector V. Abnormality is quantified as a distance x from the maximum abnormal point MAP. In the illustrated example, this gives a positive predictive value of 27/31 (87.1%).

Figure 8:
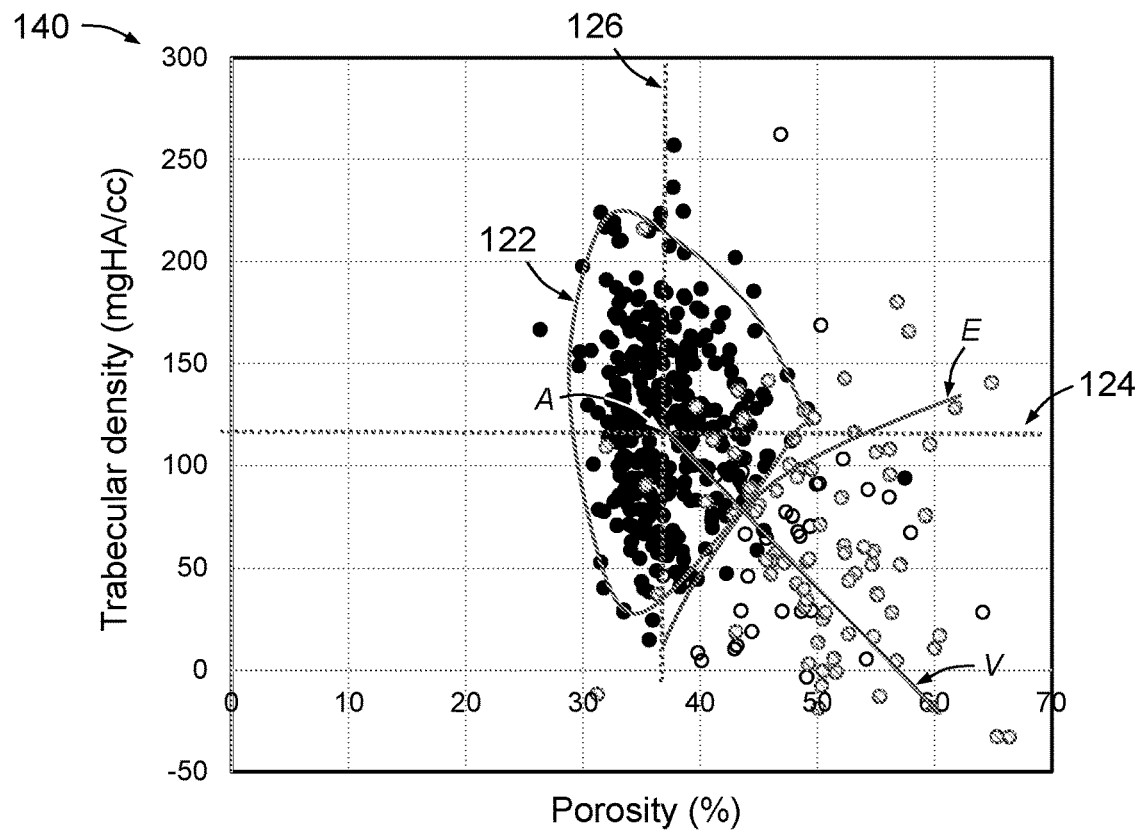
FIG. 8 illustrates the identification of abnormality according to an embodiment of the present invention, based on a definition of abnormality obtained with the abnormality quantifier builder of the system of FIG. 3A according to an embodiment of the present invention.

FIG. 8 illustrates an image 140 of a dataset that comprises the data shown in FIGS. 7A to 7D as well as data relating to an independent cohort of 77 subjects with a bone fracture (shown as shaded circles). FIG. 8 illustrates the identification of abnormality according to an embodiment of the present invention.

As in FIGS. 7A to 7D, the output or referent data are shown as hollow circles; exit vector V, derived from the analysis of image 120 of FIG. 7A is also shown in FIG. 8. The method of this embodiment, once applied to the cohort of subjects with a bone fracture, captures 57 of the 77 fracture patients as abnormal, and only 4 normal values as abnormal. This is a predictive positive value of 93.4% which is satisfactory performance.

Abnormality quantifier builder 4 has thus built an abnormality quantifier for quantifying fracture-vulnerability due to 'too little bone'. This may assist in the identification of subjects with fracture-vulnerability due to this type of abnormality so that modifying factors such as treatment can be used to decrease the level of abnormality.

When the abnormality identifier identifies an abnormality, treatment may be initiated to modify the extent of abnormality. Antiresorptives such as alendronate or denosumab, anabolic therapies such as PTH, PTHrp, and Romosozumab are known to decrease porosity and increase trabecular density. These treatments will cause the sample porosity and trabecular density to move further away from the MAP and this effect can be used to assist in the monitoring of the effectiveness of these treatments. The rate of movement of the sample relative to the MAP with time, and the magnitude of change in the spatial position of these measurements from the sample, can be used not only to assist in treatment monitoring but also to assess the differences in the effectiveness of different treatments. A more effective or more potent treatment will move samples measurements away from the MAP at a rate with time and/or at the highest magnitude.

Also, different treatments have different potencies or effectiveness. For example, anabolic therapies build bones and are more potent than antiresorptives, a greater degree of abnormality (i.e., reduction in amount of bone is severe) as quantified by this bone abnormality quantifier may help prompt the health professional to use anabolic therapies whereas a lesser degree of abnormality (the reduction in the amount of bone is less severe) may help prompt the health practitioner to use of antiresorptives instead. Thus, this abnormality quantifying may help in treatment choice.

Example 2

As in example 1, in this example the sample or population is bone is again. However, the abnormality is bone fragility (i.e., fracture-vulnerable bone), not that due to a reduced amount of bone ('too little bone' or osteoporosis) but the one due to bone with relatively normal amount but which is brittle.

Images of the bone were collected using a CT scanner. The measuring device of the abnormality quantifier builder 4 was also as for example 1: an image processor using the image processing technique disclosed in the international patent application publication no. WO 2011/029153. The processor has been preselected to automatically output bone porosity (determined as a percentage) and mineralization (determined in units as a percentage) for abnormality identifier. These measurements were preselected based on the assumption that, if the amount of bone is reduced and the mineralization level is increased then micro-cracks can initiate and propagate more easily leading to the point of catastrophic failure (i.e., fracture). Hence, these two measurements can be good markers of this type of bone fragility. If this assumption were incorrect, abnormality quantifier builder 4 would not be able to output an abnormality quantifier for this type of bone fragility by measuring these two parameters. Abnormality quantifier builder 4 would either be preset (i.e., pre-program) to measure other likely candidates measurement until an abnormality quantifier is built or the controller can input other likely candidate into the builder.

Figure 9A:
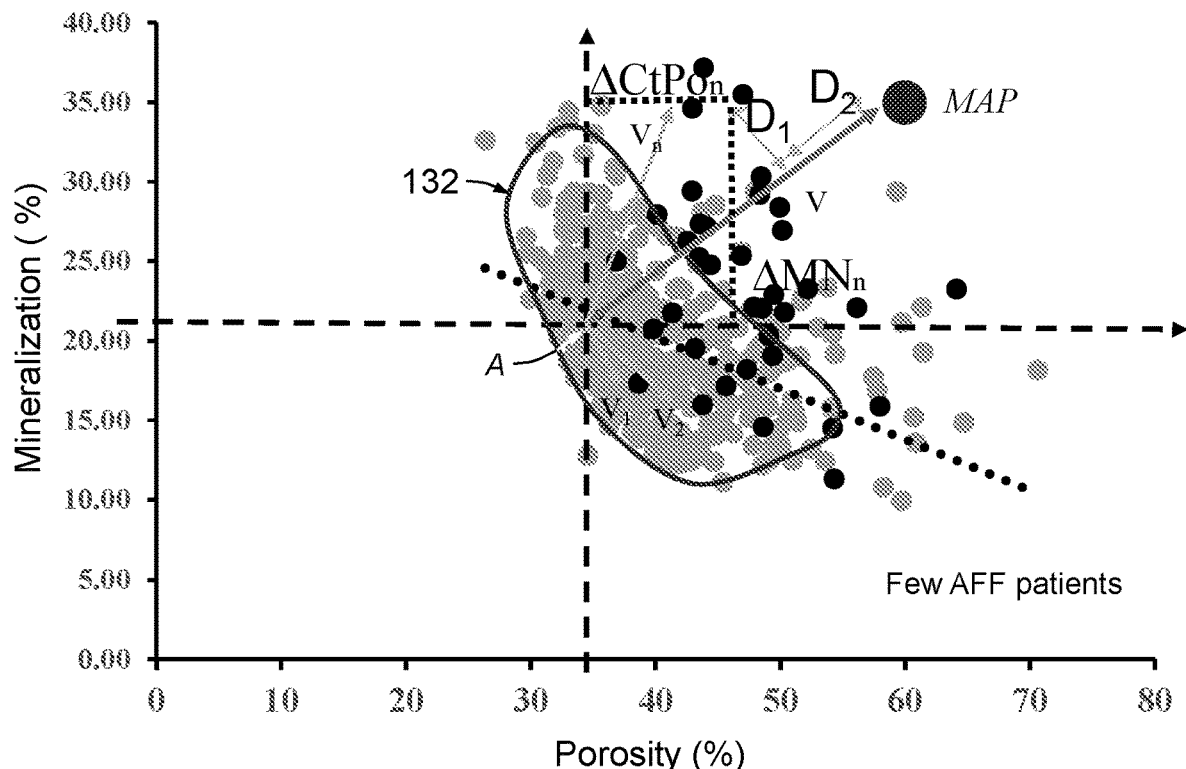
FIGS. 9A to 9C illustrate examples of an image of datasets produced using the measurements of cortical bone porosity and bone mineralization from a referent population and their analysis according to an embodiment of the present invention for determining normal and abnormal.
Figure 9B:
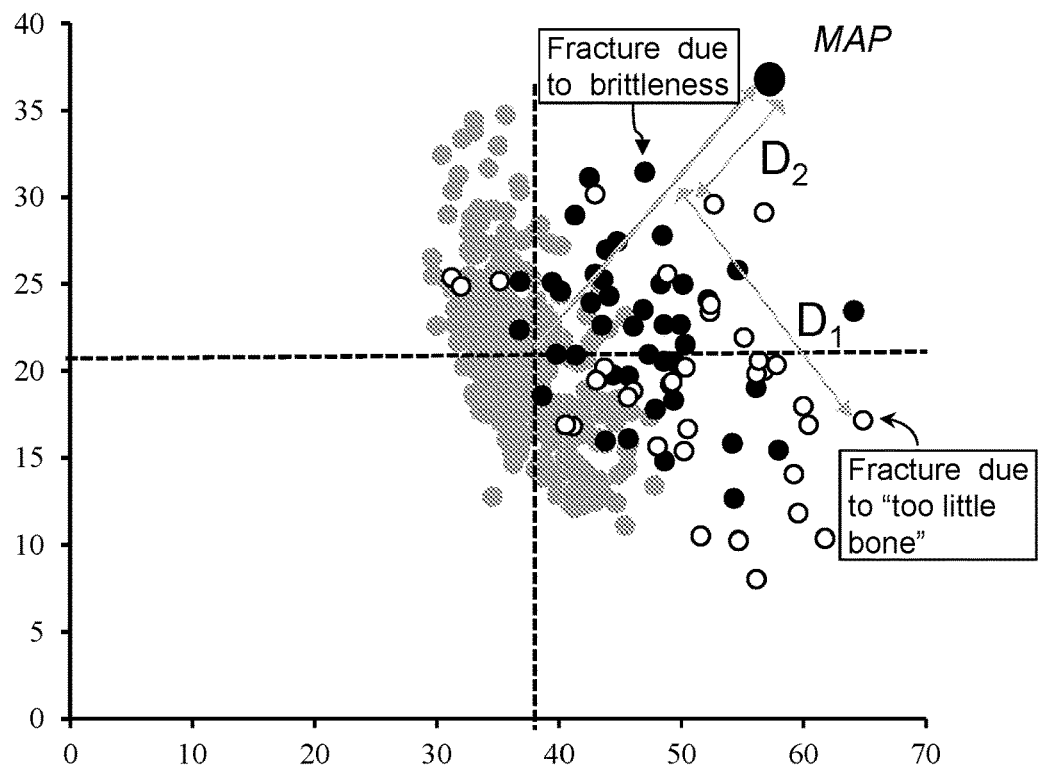
Figure 9C:
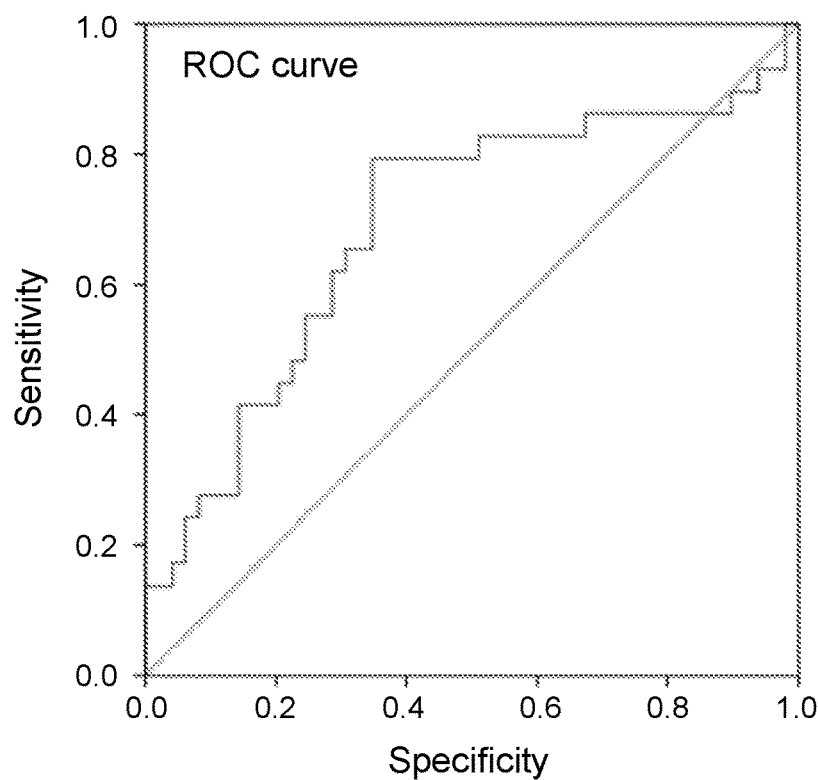

FIGS. 9A to 9C show examples of an image of datasets produced using the measurements of cortical bone porosity and bone mineralization from a referent population and their analysis according to an embodiment of the present invention for determining normal and abnormal.

Abnormality quantifier builder 4 uses a process similar to that described in example 1 to build an abnormality quantifier but for this type of bone fragility. It should however be noted that differences processes described above such as using a shape, an exit path rather than a vector could be used.

FIG. 9A is a plot of mineralization (%) (or MN) versus porosity, and depicts a quantifier of abnormality due to brittleness. In FIG. 9A, grey dots indicate normal subjects, and the normality zone is outlined by curve 132. The 'Mid normality point' A was determined as the average of porosity and mineralization from all the normal points. Mid normality point A defines four quadrants in the image, with boundaries defined by discontinued horizontal and vertical axes passing through mid normality point A.

Subjects with fractured bone due to documented bone brittleness who has sustained an unusual type of fracture none as atypical femoral fractures (AFFs), of which there are 49, are shown with dark circles: according to the present embodiment, the abnormality definer 56 uses the point in the image that corresponds to the abnormality (that is, 'mid normality point' A) to find an exit (or abnormality) vector (V). Referring to FIG. 9A, vectors V1, V2, . . . , Vn are determined as the vectors from the mid normality point A to the respective abnormal points. Exit vector V is then determined as the sum of all the vectors V1, V2, . . . , Vn; that is, V=V1+V2+ . . . +Vn.

Abnormality definer 56 then determines a maximum abnormal point (MAP), using the exit vector V. The maximum abnormal point is shown in the figure. Abnormality may then be quantified based on the magnitude of the difference between the MAP and other points.

In this embodiment, the performance of abnormality definer 56 is further tested using third datasets containing a mixture of abnormal subjects with atypical femoral fractures (due bone brittleness) and another set of abnormal subjects with this time classical or typical fracture known to be due to reduced amount of bone (see FIG. 9B). Subjects with fracture vulnerable-bone due increased brittleness and those with fracture vulnerable-bone due reduced amount of bone are of the same age. This is to ensure that the abnormality quantifier is built with enhanced performance so that it can distinguish with a reasonable degree of accuracy subjects with fracture-vulnerable bones due increases brittleness versus subjects with fracture-vulnerable bones due to reduced amount of bone "too little bone".

In FIG. 9B, it can be seeing that subjects with fracture vulnerable-bone due to reduced amount of bone are further away from the exit vector (V) as shown with the distance ($D_1$) and also further from the MAP as shown with distance ($D_2$). A simple combination of $D_1+D_2$ (denoted as material fragility score, MFS) allows to distinguish subjects with fracture-vulnerable bone due increase brittleness from those with fracture—vulnerable bone due to reduced amount with a reasonable degree of accuracy as shown by the a receiver operating characteristic (ROC), or ROC curve (FIG. 9C). It should be noted that to achieve that other combinations of $D_1$ and $D_2$ can be used.

The abnormality quantifier build by abnormality quantifier builder 4, as in Example 2, may assist in diagnosis of fracture-vulnerability, decision to treat, treatment monitoring and treatment decision. Regarding treatment decision, of particular importance is its ability to distinguish the two types of fracture-vulnerable bones.

Current approaches to identify patients with fracture-vulnerable bones, initiate treatment, and monitor treatment, are based on measurements that are composite—i.e., a mixture of the amount of bone and the material density of the matrix making that bone; therefore making them incapable to accurately determining which type of abnormality is responsible for the fracture in a subjects. These approaches include but are not limited to bone mineral density (the current gold standard for diagnosis of bone fragility), finite element analysis such as the one use for bone strength assessment; measures of bone texture, or other measured bone density at the compartmental level such as cortical density alone or trabecular density, or ultrasound based measurement of bone strength. As an example of the shortcoming of these tests, a subject with a normal amount bone that is highly mineralized to the extent of being brittle would be deemed to be normal because the average density would be either normal or high. The assumption that the higher the density, the stronger the bone which is the basis of techniques such as finite element analysis will also incorrectly suggest that the bone is stronger. In contrast, the abnormality quantifier built in the present invention will identify this bone as fracture-vulnerable due to increased brittleness regardless of its average density.

The distinction between the two types of fracture-vulnerability is important for treatment decisions. Different drugs used to treat a fracture-vulnerable bone have different effects on bone mineralization and so, may influence or change the likelihood of a bone to be brittle.

Antiresorptives such as alendronate, risedronate, or Denosumab inhibit remodelling (i.e., freeze the bone) and so allow mineralization to continue; with these drugs it is currently allowed to continue in an unchecked manner by health professional. Thus, with these drugs, mineralization may progress to the extent that the bone becomes brittle. There are indeed, documented cases of fractures due to increased brittleness in patients on antiresorptives, which are thought likely to be have been due to unwarranted changes in mineralization. The abnormality quantifier built by the builder of abnormality quantifier may assist in treatment decision when treating with antiresorptives in the following ways:

(i) if the subject is identified by the abnormality identifier to have a high level of abnormality predisposing to increase bone brittleness, then the health professional may decide not to start the subject on antiresorptives;

(ii) if the subject has already been started on antiresorptives and the abnormality identifies the subject as high level of abnormality predisposing to increase brittleness, then the health professional may decide to stop the treatment, adjust the dose of antiresorptives, or consider alternative treatments;

(iii) if during repeated measurements, when monitoring the patients the level of abnormality predisposing to increase bone brittleness shows that it is increasing, then this may assist the health professional in deciding when to stop the antiresorptive, modifying the treatment regimen (dose and/or interval of administration), or consider other treatments options before the level becomes so high that the subject is at high risk of having a fracture due to increase brittleness resulting from the antiresorptive treatment.

Anabolic therapies such a such romosozumab, teriparatide or abaloparatide form newer bone and/or remove older bone and replace it with newer bone. Whatever the case, the newer bone is less mineralized. Thus, they have the opposite effect of antiresorptives on bone mineralization. The abnormality quantifier built by the builder of abnormality quantifier may assist in treatment decision when treating with anabolic therapy in the following ways:

(i) if the subject is identified by the abnormality identifier to have a high level of abnormality predisposing to increase bone brittleness and may have a fracture due to this abnormality, then the health professional may decide start of anabolic therapy—Not antiresorptives;

(ii) if the subject has already been started on antiresorptives and the abnormality identifies the subject as having a high level of abnormality predisposing to increase brittleness, and may have had a fracture due to increase bone brittleness, then the health professional may decide to switch from antiresorptives to one of the anabolic therapies available.

By quantifying the two types of abnormality leading to a fracture-vulnerable bone, the abnormality built by the builder of abnormality quantifier offer the opportunity for a personalized medicine, and particularly in the field of bone medicine. The following are examples:

Subject 1 has a fracture due to a reduced amount of bone quantified by abnormality quantifier described in Example 1 (above). If the amount of the abnormality is not too severe, the subject may be started on antiresorptives provided the abnormality leading to increase bone brittleness quantified by the abnormality quantifier in Example 2 (above) shows that the fracture is not due to bone brittleness. However, the abnormality quantifier could be used to monitor both possible abnormalities; the existing one (reduced amount of bone) and the one likelihood to occur with treatment (increase bone brittleness). If the amount of bone is maintained or slightly increased as a result of antiresorptive therapy but the abnormality due to increase brittleness is increasing to the extent of predisposing the subject to a fracture due to increase brittleness, then the dose of antiresorptive may be adjusted, or antiresorptives may be stop, or replaced by an anabolic therapy to the extent to which the abnormality producing increased brittleness remains in a safe level. The treatment may be continued as long as required, and at the dose permissible provided this abnormality remains at the same level.

Subject 2 has a fracture due to a reduced amount of bone quantified by abnormality quantifier described in Example 1 (above). The amount the abnormality is severe. Thus, the subject may be started on anabolic therapy as the most appropriate option and when more bone has been formed by these bone forming agents, the subject may be switch to antiresorptives. When on antiresorptives, treatment dose, adjustment to treatment dose, treatment duration may be tailored based on the level of abnormality producing increase bone brittleness as quantified by abnormality quantifier of Example 2 (above).

Subjects with abnormality due to reduced amount of bone quantified by abnormality quantifier described in Example 1 are most likely to (i.) Sustain a fracture within a few years after the quantification of the abnormality (such as within 2 years) (ii.) are more likely to sustain the most severe type of fracture such as hip, vertebral, wrist or humerus fractures (iii.) are more likely to be older such as above the 70 years of age. The more severe the reduction in the amount of bone as quantified by the abnormality quantifier of Example 1, the more likely these fractures are to occur as these the fractures that are in general, associated with the most abnormality.

Subject 3 has a fracture and the abnormality is increased bone brittleness as quantified by the abnormality quantifier of Example 2. Antiresorptives increase the level of this abnormality; thus the best treatment option may be anabolic therapy which reduce the level of this abnormality. Anabolic may be started to decrease this abnormality to an extent in which it becomes safe to either stop or switch to the intervention. During treatment with anabolic therapy, the level of the abnormality leading to increase bone brittleness may be measured at designated time interval to tailor the dose of the anabolic, and its duration to the individual patient need with the target being to achieve a bone that is not at risk for fracture due to brittleness.

Bone abnormalities quantified by the abnormalities quantifier of Examples 1 and 2 provide a fundamental shift from current approaches in the diagnosis, treatment decision, treatment implementation and monitoring for bone diseases. It makes available a unique method of treatment for bone diseases. Although these examples are disclosed in the context of bone diseases similar abnormalities quantifiers can be built by the builder of abnormality quantifier for other diseases or abnormalities.

Example 3

Figure 10A:
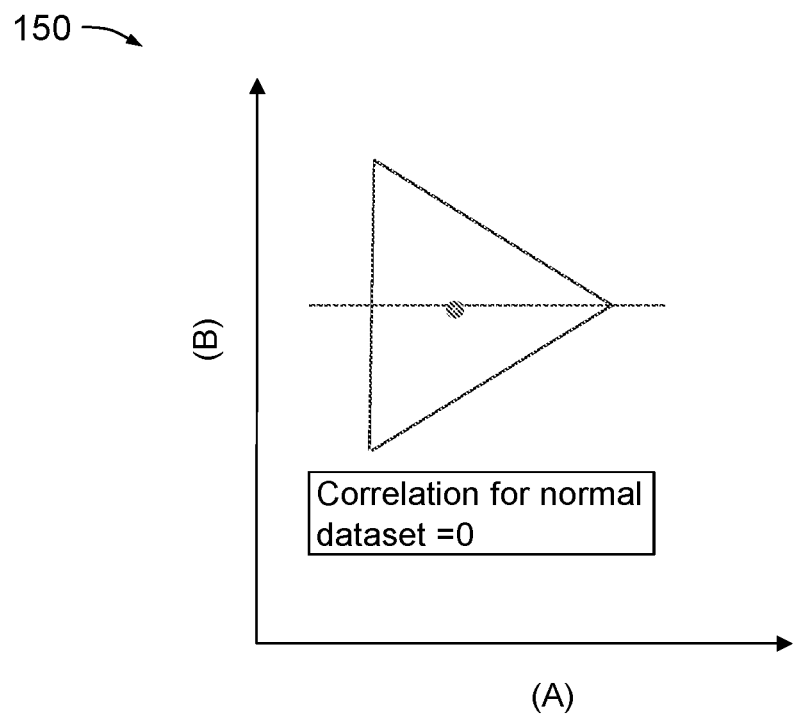
FIGS. 10A to 10C illustrate the use of the system of FIG. 3A to measure an interaction and change in the interaction between two measurements when statistical methods show no interaction as defined by the correlation coefficient not different from zero.
Figure 10B:
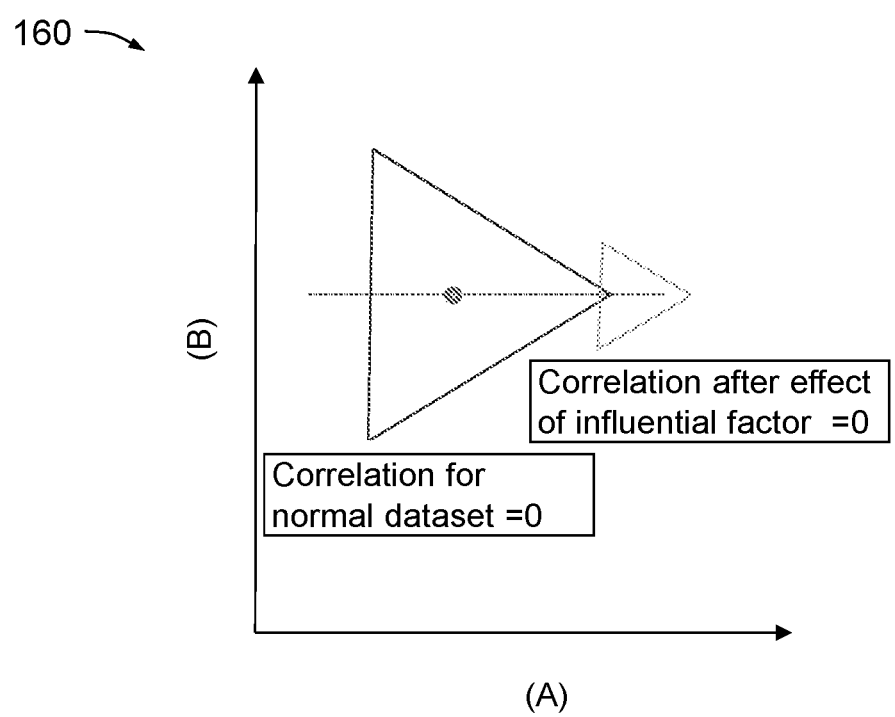
Figure 10C:
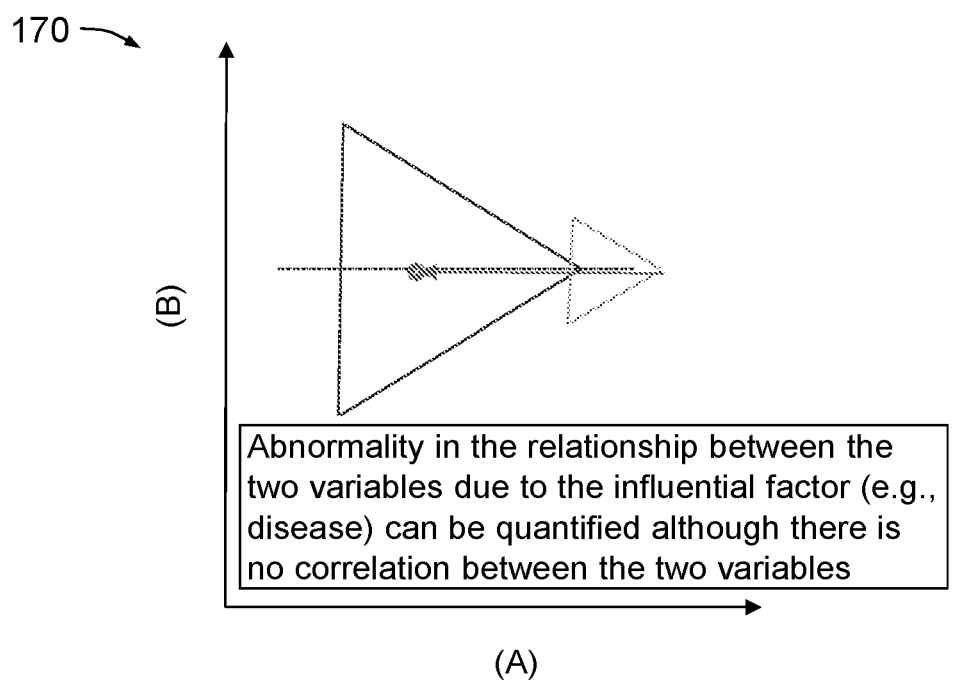

The method can be used to measure an interaction and change in the interaction between two measurements when statistical methods show no interaction as defined by the correlation coefficient not different from zero, as shown in FIGS. 10A to 10C.

The method can be used to assess the change in the interaction between two measurements (A) and (B) produced by an influential factor (such as a disease) even when the statistically the correlation between these two variables does not neither in a normal state, nor in a new state after the effect of an influential factor (e.g., Disease).

The magnitude of abnormality will still be quantified as deviation from the spatial position relative to that of the normal reference population even if the statistical parameters use to quantify the relationship between the two measurements haven't change.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The claims defining the invention are as follows:

1. A method of building an abnormality quantifier comprising:
    generating an image or map by imagizing at least one first selected dataset comprising measurements of a normal population or sample and at least one second selected dataset comprising measurements of an abnormal population or sample;
    identifying a normality zone within the image or map using the at least one first dataset;
    identifying an abnormality zone within the image or map using the at least one second dataset;
    determining a definition of normality based on the normality zone;
    determining a definition of abnormality based on a comparison of the definition of normality and the abnormality zone;
    receiving or accessing at least one third dataset comprising measurements of a both known normal and known abnormal population or sample;
    testing a performance of the determined definition of abnormality against one or more preset performance criteria;
    improving the performance by modifying one or more of the definition of normality and the definition of abnormality; and
    outputting the abnormality quantifier when a preset performance threshold has been reached;
    wherein the abnormality is disease, fracture-vulnerability of bone or obesity; and the measurements of the normal population or sample comprise co-measurements, being measurements that relate to respective characteristics of the normal population or sample, and the measurements of the abnormal population or sample comprise co-measurements, being measurements that relate to the respective characteristics of the abnormal population or sample.

2. The method as claimed in claim 1, comprising obtaining the measurements of the normal population or sample by measuring one or more normal samples or subjects, and obtaining the measurements of the abnormal population or sample by measuring one or more abnormal samples or subjects.

3. The method as claimed in claim 2, wherein measuring the one or more normal samples or subjects, or measuring the one or more abnormal samples or subjects, comprises:
    acquiring images of the samples or subjects using computed tomography (CT), magnetic resonance imaging (MRI) or other imaging device, and processing the images using an image processing technique; or
    processing previously acquired images using an image processing technique.

4. The method as claimed in claim 2, wherein measuring the one or more normal samples or subjects, or measuring the one or more abnormal samples or subjects, comprises analysing a biological sample using an analysis technique and/or obtaining measurements using a measurement instrument.

5. The method as claimed in claim 1, wherein imagizing the at least one first dataset and the at least one second dataset comprises converting geometric virtual coordinates representative of a dataset into the image or map as a cloud of points representative of normal or abnormal subjects.

6. The method as claimed in claim 1, wherein the measurements of the normal population or sample and measurements of the abnormal population or sample are made with an imaging device configured to output a plurality of different sets of bone parameters.

7. The method as claimed as claim 6, wherein the abnormality is the fracture-vulnerability of bone that is due to structural abnormality comprising a reduced amount of the bone.

8. The method as claimed in claim 7, further comprising estimating a timeframe in which a fracture may occur from the amount of the bone reduction.

9. The method as claimed in claim 7, further comprising recategorizing a subject previously categorized by adjusting the definition of abnormality.

10. The method as claimed in claim 1, wherein the abnormality is age dependent.

11. The method as claimed in claim 1, further comprising determining a type of the fracture-vulnerability of bone including distinguishing fracture-vulnerability due to reduced amount of the bone from fracture-vulnerability due to bone brittleness.

12. The method as claimed in claim 1, wherein the abnormality is bone disease, bone fragility due to osteoporosis, or bone fragility due to bone brittleness.

13. A computer-implemented method for identifying abnormality in one or more measurements; of a population or sample, the method comprising:
   receiving or accessing a definition of abnormality generated according to a method comprising:
   a) generating an image or map by imagizing at least one first dataset comprising measurements of a normal population or sample and at least one second dataset comprising measurements of an abnormal population or sample;
   b) identifying a normality zone within the image or map using the at least one first dataset;
   c) identifying an abnormality zone within the image or map using the at least one second dataset;
   d) determining a definition of normality based on the normality zone;
   e) determining a definition of abnormality based on a comparison of the definition of normality and the abnormality zone;
   f) testing a performance of the determined definition of abnormality against one or more preset performance criteria, using at least one third dataset comprising measurements of a both known normal and known abnormal population or sample; and
   g) improving the performance by modifying one or more of the definition of normality and the definition of abnormality;
   determining from the definition of abnormality which of the one or more measurements of the population sample correspond to abnormality;
   wherein the abnormality is disease, fracture-vulnerability of bone or obesity; and the measurements of the normal population or sample comprise co-measurements, being measurements that relate to respective characteristics of the normal population or sample, and the measurements of the abnormal population or sample comprise co-measurements, being measurements that relate to the respective characteristics of the abnormal population or sample.

14. The computer-implemented method as claimed in claim 13, wherein imagizing the at least one first dataset and the at least one second dataset comprises converting geometric virtual coordinates representative of a dataset into the image or map as a cloud of points representative of normal or abnormal subjects.

15. A non-transient computer readable medium, comprising executable instructions or software that, when executed by a computing device or processor of a computing device, cause the computing device or processor to perform the method of claim 13.

16. The method as claimed in claim 13, wherein the abnormality is bone disease, bone fragility due to osteoporosis, or bone fragility due to bone brittleness.

17. The method as claimed in claim 13, further comprising identifying one or more abnormalities in the one or more measurements of the population or sample that correspond to the abnormality.

18. The method as claimed in claim 17, further comprising applying, designing or modifying a treatment based on the one or more abnormalities.

19. An apparatus for identifying abnormality in one or more measurements of a population or sample, comprising:
   a processor;
   a memory; and
   an outputter;
   wherein the processor is configured to generate an image or map by imagizing at least a first and a second dataset, the first dataset comprising measurements of a normal population or sample and the second dataset comprising measurements of an abnormal population or sample;
   to identify a normality zone within the image or map using the first dataset and identify an abnormality zone within the image or map using the second dataset;
   to determine a definition of normality based on the normality zone;
   to determine a definition of abnormality based on a comparison of the definition of normality and the abnormality zone, to test a performance of the determined definition of abnormality against one or more preset performance criteria using at least one third dataset comprising measurements of a both known normal and known abnormal population or sample, and to improve the performance by modifying one or more of the definition of normality and the definition of abnormality;
   wherein the outputter is configured to output at least one result; and
   the abnormality is disease, fracture-vulnerability of bone or obesity; and the first and second datasets comprise co-measurements, the measurements of the normal population or sample being measurements that relate to respective characteristics of the normal population or sample, and the measurements of the abnormal population or sample being measurements that relate to the respective characteristics of the abnormal population or sample.

20. The apparatus as claimed in claim 19, wherein imagizing the at least one first dataset and the at least one second dataset comprises converting geometric virtual coordinates representative of a dataset into the image or map as a cloud of points representative of normal or abnormal subjects.

21. The apparatus as claimed in claim 19, wherein the & normality definer is configured to determine a definition of normality using spatial characteristics of the normality zone.

22. The apparatus as claimed in claim 19, including a binarizer.

23. The apparatus as claimed in claim 19, wherein the abnormality is bone disease, bone fragility due to osteoporosis, or bone fragility due to bone brittleness.

24. A method of building an abnormality quantifier comprising:
   generating an image or map by imagizing at least one first selected dataset comprising measurements of a normal population or sample and at least one second selected dataset comprising measurements of an abnormal population or sample;
   identifying a normality zone within the image or map using the at least one first dataset;
   identifying an abnormality zone within the image or map using the at least one second dataset;
   determining a definition of normality based on the normality zone;

determining a definition of abnormality based on a comparison of the definition of normality and the abnormality zone;

receiving or accessing at least one third dataset comprising measurements of a both known normal and known abnormal population or sample; and testing a performance of the determined definition of abnormality against one or more preset performance criteria;

outputting the abnormality quantifier when a preset performance threshold has been reached;

wherein the measurements of the normal population or sample comprise co-measurements, being measurements that relate to respective characteristics of the normal population or sample, and the measurements of the abnormal population or sample comprise co-measurements, being measurements that relate to the respective characteristics of the abnormal population or sample;

the population or sample comprises bone;

the measurements of the normal population or sample and the measurements of the abnormal population or sample are made with an imaging device configured to output a plurality of different sets of bone parameters;

the abnormality is fracture-vulnerability due to structural abnormality comprising a reduced amount of bone; and the method further comprises estimating a timeframe in which a fracture may occur from an amount of bone reduction.

* * * * *